(12) United States Patent
Hazen et al.

(10) Patent No.: US 9,581,597 B2
(45) Date of Patent: *Feb. 28, 2017

(54) MYELOPEROXIDASE, A RISK INDICATOR FOR CARDIOVASCULAR DISEASE

(71) Applicant: THE CLEVELAND CLINIC FOUNDATION, Cleveland, OH (US)

(72) Inventors: Stanley L. Hazen, Pepper Pike, OH (US); Renliang Zhang, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/135,757

(22) Filed: Apr. 22, 2016

(65) Prior Publication Data

US 2016/0238605 A1 Aug. 18, 2016

Related U.S. Application Data

(63) Continuation of application No. 14/591,381, filed on Jan. 7, 2015, which is a continuation of application No. 11/753,799, filed on May 25, 2007, now Pat. No. 9,170,260, which is a continuation of application No. 10/039,753, filed on Jan. 2, 2002, now Pat. No. 7,223,552.

(60) Provisional application No. 60/259,340, filed on Jan. 2, 2001, provisional application No. 60/283,432, filed on Apr. 12, 2001.

(51) Int. Cl.
| | |
|---|---|
| *C12Q 1/28* | (2006.01) |
| *G01N 37/00* | (2006.01) |
| *G01N 33/573* | (2006.01) |
| *G06F 19/00* | (2011.01) |
| *G06Q 50/22* | (2012.01) |
| *C12N 1/28* | (2006.01) |
| *A61K 31/616* | (2006.01) |

(52) U.S. Cl.
CPC ......... *G01N 33/573* (2013.01); *A61K 31/616* (2013.01); *C12N 1/28* (2013.01); *C12Q 1/28* (2013.01); *G06F 19/3431* (2013.01); *G06Q 50/22* (2013.01); *C12Y 111/01007* (2013.01); *G01N 2333/908* (2013.01); *G01N 2800/32* (2013.01); *G01N 2800/324* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2,765,299 A | 10/1956 | Porsche et al. | |
| 5,122,534 A | 6/1992 | Loose et al. | |
| 5,460,961 A * | 10/1995 | Deby | C12N 9/0065 424/417 |
| 5,731,208 A | 3/1998 | Heinecke | |
| 5,747,274 A | 5/1998 | Jackowski | |
| 5,776,892 A | 7/1998 | Counts et al. | |
| 5,789,178 A * | 8/1998 | Moyle | C07K 16/18 435/7.1 |
| 5,846,959 A | 12/1998 | Medford et al. | |
| 5,871,946 A | 2/1999 | Lucas et al. | |
| 5,874,313 A | 2/1999 | Ahotupa | |
| 5,889,042 A | 3/1999 | Maclean et al. | |

(Continued)

FOREIGN PATENT DOCUMENTS

| | | |
|---|---|---|
| EP | 0389381 | 3/1990 |
| EP | 0418486 | 7/1990 |

(Continued)

OTHER PUBLICATIONS

Deby-Dupont et al. "Equine neutrophil myeloperoxidase in plasma: design of a radio-immunoassay and first results in septic pathologies" Veterinary Immunology and Immunopathology 66 (1998) 257-271.*
Xia and Zweier, "Measurement of Myeloperoxidase in Leukocyte-containing tissues" Analytical Biochemistry 245, 93-96 (1997).*
Faymonville et al. "Myeloperoxidase and elastase as markers of leukocyte activation during cardiopulmonary bypass in humans" J Thorac Cardiovasc Surg 1991; 102: 309-17.*
Abernethy et al., "Calcium-Antagonist Drugs," NEJM, (1999) 341: 1447-1457.
Carr et al., "Oxidation of LDL by Myeloperoxidase and Reactive Nitrogen Species," Arterioscler. Thromb. Vasc. Biol., (2000) 20: 1716-1723.
Holvoet et al., "Oxidized Low Density Lipoproteins in Patients with Transplant-Associated Coronary Artery Disease," Arterioscler. Thromb. Vasc. Biol., (1998) 18: 100-107.

(Continued)

*Primary Examiner* — Daniel E Kolker
*Assistant Examiner* — James Rogers
(74) *Attorney, Agent, or Firm* — Tarolli, Sundheim, Covell & Tummino LLP

(57) ABSTRACT

Diagnostic tests for characterizing an individual's risk of developing or having a cardiovascular disease. In one embodiment the present diagnostic test comprises determining the level of myeloperoxidase (MPO) activity in a bodily sample obtained from the individual or test subject. In another embodiment, the diagnostic test comprises determining the level of MPO mass in a bodily sample obtained from the test subject. In another embodiment, the diagnostic test comprises determining the level of one or more select MPO-generated oxidation products in a bodily sample obtained from the test subject. The select MPO-generated oxidation products are dityrosine, nitrotyrosine, methionine sulphoxide or an MPO-generated lipid peroxidation products. Levels of MPO activity, MPO mass, or the select MPO-generated oxidation product in bodily samples from the test subject are then compared to a predetermined value that is derived from measurements of MPO activity, MPO mass, or the select MPO-generated oxidation product in comparable bodily samples obtained from the general population or a select population of human subjects. Such comparison characterizes the test subject's risk of developing CVD.

2 Claims, 11 Drawing Sheets

(56) References Cited

U.S. PATENT DOCUMENTS

| | | | |
|---|---|---|---|
| 5,985,272 | A | 11/1999 | Deby et al. |
| 6,096,556 | A | 8/2000 | Heinecke |
| 6,133,039 | A | 10/2000 | Heinecke |
| 6,268,220 | B1 | 7/2001 | Heinecke |
| 6,599,713 | B1 * | 7/2003 | Hatanaka ............... C12Q 1/28 435/28 |
| 6,893,829 | B2 | 5/2005 | Nadler et al. |
| 6,953,666 | B1 | 10/2005 | Kinkade, Jr. et al. |
| 7,030,152 | B1 | 4/2006 | Ridker et al. |
| 7,223,552 | B2 | 5/2007 | Hazen et al. |
| 2002/0156007 | A1 | 10/2002 | Graversen et al. |
| 2002/0164662 | A1 | 11/2002 | Hazen et al. |
| 2003/0008373 | A1 | 1/2003 | Bartel et al. |
| 2003/0119792 | A1 | 6/2003 | Roca |
| 2004/0029807 | A9 | 2/2004 | Dasseux et al. |
| 2004/0115749 | A1 | 6/2004 | Buchanan |
| 2008/0009020 | A1 | 1/2008 | Hazen et al. |
| 2011/0152224 | A1 | 6/2011 | Hazen et al. |
| 2012/0129708 | A1 | 5/2012 | Bale et al. |

FOREIGN PATENT DOCUMENTS

| | | |
|---|---|---|
| WO | 96/04311 | 2/1996 |
| WO | 9810294 A1 | 3/1998 |
| WO | 02/48715 | 6/2002 |
| WO | 02/50550 | 6/2002 |
| WO | 02/062207 | 8/2002 |

OTHER PUBLICATIONS

Holvoet et al., "Oxidized LDL and Malondialdehyde-Modified LDL in Patients with Acute Coronary Syndromes and Stable Coronary Artery Disease," Circulation, (1998) 98: 1487-1494.
Holvoet et al., "Oxidized Low Density Lipoprotein is a Prognostic Marker of Transplant-Associated Coronary Artery Disease," Arterioscler. Thromb. Vasc. Biol., (2000) 20: 698-702.
Kohno et al., "Simple and Practical Sandwich-Type Enzyme Immunoassay for Human Oxidatively Modified Low Density Lipoprotein Using Antioxidized Phosphatidylcholine Monoclonal Antibody and Antihuman Apolipoprotein-B Antibody," Clin. Biochem., (2000) 33: 243-253.
Maseri et al., "Pathogenic Mechanisms in Unstable Angina," Heart, (1999) 82(Supplement I): 12-14.
Terletskaya, "Alkaline Phosphatase and Myeloperoxidase of Granulocytes in Patients with Ischemic Heart Disease," Vrach Delo, (1989) 3: 13-14.
Terletskaya, "Alkaline Phosphatase and Myeloperoxidase of Granulocytes in Patients with Ischemic Heart Disease," Vrach Delo, (1989) 3: 13-14. (English Translation).
Toshima et al., "Circulating Oxidized Low Density Lipoprotein Levels," Arterioscler. Thromb. Vasc. Biol., (2000), 20: 2243-2247.
First Request for Ex Parle Reexamination of U.S. Pat. No. 7,223,552 82, U.S. Appl. No. 10/039,753 (parent application of instant U.S. Appl. No. 11/753,799), filed Jun. 18, 2009.
Encyclopedia entry for abdominal aortic aneurysm, Medline Plus Medical Encyclopedia, http://www.nlm.nih.gov/medlineplus/ency/article/000162.htm.
Definition of angina pectoris, Wikipedia, http://en.wikipedia.org/wiki/Angina_pectoris.
Definition of atherosclerosis, The American Heritage Stedman's Medical Dictionary, Houghton Mifflin Company (2001), p. 72.
Definition of atherosclerosis, Wikipedia, http://en.wikipedia.org/wiki/Atherosclerosis.
Definition of white blood cell, Wikipedia, http://en.wikipedia.org/wiki/White_blood_cell.
Order Granting First Request for Ex Parle Reexamination of U.S. Pat. No. 7,223,552 82, U.S. Appl. No. 10/039,753 (parent application of instant U.S. Appl. No. 111753,799), mailed Aug. 12, 2009.
Examiner Interview Summary from First Ex Parle Reexamination of U.S. Pat. No. 7,223,552 82, U.S. Appl. No. 10/039,753 (parent application of instant U.S. Appl. No. 111753,799), mailed Dec. 15, 2009.
Preliminary Amendment from First Ex Parle Reexamination of U.S. Pat. No. 7,223,552 82, U.S. Appl. No. 10/039,753 (parent application of instant U.S. Appl. No. 111753,799), filed Jan. 4, 2010.
Applicant Summary of the Interview with the Examiner from First Ex Parle Reexamination of U.S. Pat. No. 7,223,552 82, U.S. Appl. No. 10/039,753 (parent application of instant U.S. Appl. No. 111753,799), filed Jan. 4, 2010.
Notice of Intent to Issue Reexamination Certificate from First Ex Parle Reexamination of U.S. Pat. No. 7,223,552 82, U.S. Appl. No. 10/039,753 (parent application of instant U.S. Appl. No. 111753,799), mailed Jan. 29, 2010.
Reexamination Certificate from First Ex Parle Reexamination of U.S. Pat. No. 7,223,552 82, U.S. Appl. No. 10/039,753 (parent application of instant U.S. Appl. No. 111753,799), issued May 4, 2010.
Second Request for Ex Parle Reexamination of U.S. Pat. No. 7,223,552 82, U.S. Appl. No. 10/039,753 (parent application of instant U.S. Appl. No. 111753,799), filed May 11, 2010.
Declaration of Luigi M. Biasucci submitted with Second Request for Ex Parle Reexamination of U.S. Pat. No. 7,223,552 82, U.S. Appl. No. 10/039,753 (parent application of instant U.S. Appl. No. 111753,799), dated May 11, 2010.
Order Granting Second Request for Ex Parle Reexamination of U.S. Pat. No. 7,223,552 82, U.S. Appl. No. 10/039,753 (parent application of instant U.S. Appl. No. 111753,799), mailed Jul. 27, 2010.
Non-final Office Action from Second Request for Ex Parle Reexamination of U.S. Pat. No. 7,223,552 82, U.S. Appl. No. 10/039,753 (parent application of instant U.S. Appl. No. 11/753,799), mailed Dec. 2, 2010.
Examiner Interview Summary from Second Ex Parle Reexamination of U.S. Pat. No. 7,223,552 82, U.S. Appl. No. 10/039,753 (parent application of instant U.S. Appl. No. 111753,799), mailed Jan. 20, 2011.
Response to Non-final Office Action from Second Request for Ex Parle Reexamination of U.S. Pat. No. 7,223,552 82, U.S. Appl. No. 10/039,753 (parent application of instant U.S. Appl. No. 11/753,799), filed Feb. 2, 2011.
Supplemental Response to Non-final Office Action from Second Request for Ex Parle Reexamination of U.S. Pat. No. 7,223,552 82, U.S. Appl. No. 10/039,753 (parent application of instant U.S. Appl. No. 111753,799), filed Feb. 15, 2011.
Hazen et al., "Elevated levels of protein-bound p-hydroxyphenylacetaldehyde, an amino acid-derived aldehyde generated by myeloperoxidase, are present in human fatty streaks, intermediate lesions and advanced atherosclerosis lesions", Biochem J., 352, p. 693-699 (2000).
Heinecke et al., "Mass spectrometric quantification of amino acid oxidation products in proteins: insights into pathways that promote LDL oxidation in the human artery wall", FASEB J., 13, p. 1113-1120 (1999).
Leeuwenburgh et al., "Reactive Nitrogen Intermediates Promote Low Density Lipoprotein Oxidation in Human Atherosclerotic Intima", The Journal of Biological Chemistry, vol. 272, pp. 1433-1436 (1997).
Malech et al., "Primary inherited Defects in Neutrophil function: Etiology and Treatment", Seminars in Hematology, 34, p. 279-290 (1997).
Sacks et al., "The effect of Pravastatin on Coronary Events after Myocardial Infarction in Patients with Average Cholesterol Levels", The New England Journal of Medicine, vol. 335, pp. 1001-1009. Oct. 3, 1996.
Schwemmer et al., "How urine analysis reflects oxidative stress—nitrotyrosine as a potential marker", Clninica Chimica Acta, 297, p. 207-216 (2000).
Febbraio et al., "Targeted disruption of the class B scavenger receptor CD36 protects against atherosclerotic lesion development in mice", J. Clin. Invest., 105, p. 1049-1056 (2000).
Heinecke, J.W., "Oxidants and antioxidants in the pathogenesis of atherosclerosis: implications for the oxidized low density lipoprotein hypothesis", Atherosclerosis, p. 1-15 (1998).

(56) References Cited

OTHER PUBLICATIONS

Tang et al., "Arginine methylation index as integrated quantification of arginine methylation provides stronger independent risk prediction of long-term cardiovascular events than individual methylated arginine metabolites," Circulation, 118, S564 (2008).
Wang et al., "Analysis of multiple methylation derivatives of amino acids suggests that factors independent of nitric oxide synthase inhibition are responsible for their prognostic value for cardiovascular risk prediction," J. Am. Coll.
Marathe, G. K. et al., "Bioactive phospholipid oxidation products." Free Radie. Biol. Med. 28: 1762-1770; 2000.
Meagher, E. A. et al., "Indices of lipid peroxidation in vivo: strengths and limitations". Free Radie. Biol. Med. 28: 17451750; 2000.
Subbanagounder, G."Bioactive products of phospholipid oxidation: isolation, identification, measurement and activities." Free Radie. Biol. Med. 28: 17511761; 2000.
Thukkani et al., "Identification of a-Chloro Fatty Aldehydes and Unsaturated Lysophosphatidylcholine Molecular Species in Human Atherosclerotic Lesions", Circulation, Dec. 23-30, 2003, pp. 3128-3133.
Shishehbor et al., "Systemic elevations of free radical oxidation products of arachidonic acid are associated with angiographic evidence of coronary artery disease", Free Radical Biology & Medicine 41, pp. 1678-1683 (2006).
Podrez et al., "Platelet CD36 links hyperlipidemia, oxidant stress and a prothrombotic phenotype", Nature Medicine, vol. 13, No. 9, pp. 1086-1095, Sep. 2007.
Hazen et al., "Oxidized Phospholipids as Endogenous Pattern Recognition Ligands in Innate Immunity", J of Biological Chemistry, vol. 283, No. 23, pp. 15227-15337, Jun. 6, 2008.
Diaz et al., "Antioxidants and atherosclerotic heart disease", N Engl J Med 337: 408-416 (1997).
Hazen et al., "Synthesis, isolation and characterization of the adduct formed in the reaction of p-hydroxyphenylacetaldehyde with the amino head group of phosphatidyl ethanolamine and phosphatidylserine", Chem Res Toxicol 12: 19-27 (1999b).
Hazen, et al., "Formation of Nitric-Oxide Derived Oxidants by Myeloperoxidase in Monocytes, Pathways for Monocyte-Mediated Protein Nitration and Lipid Peroxidation In Vivo", Circ. Res. 1999;85:950-958.
International Search Report dated Nov. 27, 2007 from PCT/US05/27801.
Sugiyama et al., Macrophage myeloperoxidase regulation by granulocyte macrophage colony-stimulating factor in human atherosclerosis and implations in acute coronary syndromes, Am J Pathol 158: 879-891 (2001).
Thomas et al., "Molecular action of vitamin E in lipoprotein oxidation: Implication for atherosclerosis", Free Radie Biol Med 28: 1795-1805 (2000).
Wiltztum et al., "The oxidative modification hypothesis of atherosclerosis: does ii hold for humans?", Trends Cardiovasc Med 11:93-102 (2001).
Zhang et al., "The role of myeloperoxidase in the initiation of lipid peroxidalion in plasma as studies in neutrophils isolated from myeloperoxidase deficient subjects: Sytstematic approach to the identification and characterization of multiple diffusible endogenous substrates for myeloperoxidase in plasma", Blood 99: pp. 802-1810 (2002b).
Davi et al., "Increased levelas of soluble P-selectin in hypercholesterolemic patients", Circulation, vol. 97, pp. 953-957 (1998).
Berliner et al., "A role for oxidized phospholipids in atherosclerosis", N Engl J Med, vol. 353, pp. 9-11 (2005).
Podrez et al., "Identification of a novel family of oxidized phospholipids that serve as ligands for the macrophage scavenger receptor CD36", J Biol Chem, vol. 277, pp. 38503-38516 (2002).
Podrez et al., "A novel family of atherogenic oxidized phospholipids promotes macrophage foam cell formation via the scavenger receptor CD 36 and is enriched in atherosclerotic lesions", J Biol Chem, vol. 277, 38517-38523 (2002).
Fabbraio et al., "CD36: a class B scavenger receptor involved in angiogenesis, atherosclerosis, inftammation, and lipid metabolism", J Clin Invest vol. 108, pp. 785-791 (2001).
Berliner et al., "Atherosclerosis: basic mechanisms, Oxidation, inflammation, and genetics", Circulation 91, 9, pp. 2488-2496 (1995).
Berliner et al.. "Oxidized lipids in atherogenesis: formation, destruction and action", Thromb Haemost, vol. 78, 1, p. 195-199 (1997).
Navab et al., "The Yin and Yang of oxidation in the development of the fatty streak. A review based on the 1994 George Lyman Duff Memorial Lecture", Arterioscler. Thromb Vase Biol, 16, 7, pp. 831-842 (1996).
Hazen, S.L., "Oxidation and atherosclerosis", Free Radie Biol Med, 28, 12, pp. 1683-1684 (2000).
Loscalzo, J., "Oxidative stress in endothelial cell dysfunction and thrombosis", Pathophysiol Haemost Thromb, 32, 5-6, pp. 359-360 (2002).
Harrison, D., "Oxidative stress and coronary artery disease", Can J Cardiol 14, 30D-32D (Suppl D), 1998.
Vivekenanthan et al., "Use of antioxidant vitamins for the prevention of cardiovascular disease: meta-analysis of randomised trials", Lancet 361, 9374, pp. 2017-2023 (2003).
Shishehbor et al., "Inftammatory and oxidative markers in atherosclerosis: relationalship to outcome", Curr Atheroscler Rep, 6, 3, pp. 243-250 (2004).
Shishehbor et al., "Antioxidant studies need a change of direction", Cleve Clin J Med vol. 71, No. 4, pp. 285-288 (2004).
Brennan et al., "Emerging role of myeloperoxidase and oxidant stress markers in cardiovascular risk assessment", Curr Opin Lipidol, vol. 14, No. 4, pp. 353-359 (2003).
Morrow, J.D., "Quantification of isoprostanes as indices of oxidant stress and the risk of atherosclerosis in humans", Arterioscler Thromb Vase Biol, vol. 25, No. 2, pp. 279-286 (2005).
Shishehbor et al., "Statins promote potent systemic antioxidant effects through specific inftammatory pathways", Circulation, vol. 108, No. 4, pp. 426-431 (2003).
Schutlz et al.. "Quest for fire: seeking the source of pathogenic oxygen radicals in atherosclerosis", Arterioscler Thromb Vase Biol 20, 6, pp. 1412-1413 (2000).
Nicholls et al., "Myeloperoxidase and cardiovascular disease", Arterioscler Thromb Vase Biol vol. 25, No. 6, pp. 1102-1111 (2005).
Maegher et al., "Effects of vitamin E on lipid peroxidation in healthy persons", JAMA, vol. 285, No. 9, pp. 1178-1 (2001).
Savenkova et al., "Tyrosyl radical generated by myeloperoxidase is a physiological catalyst for the initiation of lipid peroxidation in low density lipoprotein", J Biol Chem vol. 269, No. 32, pp. 20394-20400 (1994).
Lawson et al., "Isoprostanes: formation, analysis and use as indices of lipid peroxidation in vivo", J Biol Chem, vol. 274, No. 35, pp. 24441-24444 (1999).
Practico et al., "Localization of distinct F2-isoprostanes in human atherosclerotic lesions", J Clin Invest, vol. 100, No. 8, pp. 2028-2034 (1997).
Reilly et al., "Increased formation of distinct F2 isoprostanes in hypercholesterolemia", Circulation 98 (25), 2822-2828 (1998).
Mallat et al., "The relationship of hydroxyeicosatetraenoic acids and F2-isoprostanes to plaque instability in human carotid atherosclerosis", J Clin Invest vol. 103, No. 3, pp. 421-427 (1999).
Spidle et al., "Oxidative stress and inflammation in hemodialysis patients", Am J Kidney Dis, vol. 38, No. 6, pp. 1408-1413 (2001).
Morrow et al., "Increase in circulating products of lipid peroxidation (F2-isoprostanes) in smokers. Smoking as a cause of oxidative damage", N Engl J Med vol. 332, No. 18, pp. 1198-1203 (1995).
Office Action from U.S. Appl. No. 11/313,012 dated Sep. 21, 2007.
Response from U.S. Appl. No. 11/313,012 dated Mar. 19, 2008.
Final Office Action from U.S. Appl. No. 11/313,012 dated Aug. 19, 2008.
Response to Final Office action from U.S. Appl. No. 11/313,012 dated Jan. 21, 2009.
Office Action from U.S. Appl. No. 10/039,753 dated Mar. 24, 2005.

(56) References Cited

OTHER PUBLICATIONS

Response from U.S. Appl. No. 10/039,753 dated Jun. 22, 2005.
Office action from U.S. Appl. No. 10/039,753 dated Sep. 8, 2005.
Response from U.S. Appl. No. 10/039,753 dated Nov. 30, 2005.
Office Action from U.S. Appl. No. 10/039,753 dated Mar. 10, 2006.
Response from U.S. Appl. No. 10/039,753 dated Apr. 7, 2006.
Interview Summary from U.S. Appl. No. 10/039,753 dated Apr. 14, 2006.
Statement of the Substance of the Interview from U.S. Appl. No. 10/039,753 dated May 3, 2006.
Final Office Action from U.S. Appl. No. 10/039,753 dated Jul. 3, 2006.
Response from U.S. Appl. No. 10/039,753 dated Jul. 26, 2006.
Office Action from U.S. Appl. No. 10/039,753 dated Aug. 17, 2006.
Response from U.S. Appl. No. 10/039,753 dated Sep. 6, 2006.
Final Office Action from U.S. Appl. No. 10/039,753 dated Nov. 22, 2006.
Response from U.S. Appl. No. 10/039,753 dated Dec. 7, 2006.
Advisory Action from U.S. Appl. No. 10/039,753 dated Dec. 28, 2006.
Response from U.S. Appl. No. 10/039,753 dated Jan. 3, 2007.
Advisory Action from U.S. Appl. No. 10/039,753 dated Feb. 21, 2007.
Response from U.S. Appl. No. 10/039,753 dated Feb. 28, 2007.
Interview Summary from U.S. Appl. No. 10/039,753 dated Mar. 2, 2007.
Notice of Allowance from U.S. Appl. No. 10/039,753 dated Mar. 19, 2007.
Mertens, et al., "Oxidized LDL and HDL: antagonists in atherothrombosis," FASEB J., vol. 15, 2073-2084 (2001).
Minota et al., "Circulating Myeloperoxidase and Anti-Myeloperoxidase Antibody in Patients with Vasculitis," Scand J. Rheumatol, 1999;25:94-9.
Momii et al., "Inhibition of Adhesion Molecules Markedly Ameliorates Cytokine-Induced Sustained Myocardial Dysfunction in Dogs in vivo," J. Mal. Cell. Cardiel. vol. 30, 2637-2650 (1998).
Moriel et al., "Nitrotyrosine Bound to JI-VLDL-Apoproteins: A Biomarker of Peroxynitrite Formation in Experimental Atherosclerosis," Biochemical and Biophysical Research Communications vol. 232, pp. 332-335 (1997).
Naruko et al., "Neutrophil Infiltration of Culprit Lesions in Acute Coronary Syndromes," Circulation, 2002; 106:2894-2900.
Nauseef. "Myeloperoxidase Deficiency," Hematology, Oncology Clinics of North America, vol. 2, No. 1, Mar. 1988, pp. 135-158.
Novaro et al., "Effect of Hydroxymethylglutaryl Coenzyme A Reductase Inhibitors on the Progression of Calcific Aortic Stenosis," Circulation, 2001; 104:2205-2209.
Podrez et al. "Macrophage scavenger receptor CD36 is the major receptor for LDL modified by monocyte-generaled reactive nitrogen species," J. Clin. Ives!. vol. 105:1095-1108 (2000).
Podrez et al., "Myeloperoxidase-General ed Oxidants and Atherosclerosis," Free Radical Biology & Medicine, vol. 28, No. 12, pp. 1717-1725, Jan. 2000.
Podrez et al., "Myeloperoxidase-general ed reactive nitrogen species convert LDL into an atherogenic form in vitro," J. Clin. Invest. vol. 103, pp. 1547-1560 (1999).
Ridker et al. "Measurement of C-Reactive Protein for the Targeting of Stalin Therapy in the Primary Prevention of Acute Coronary Events," The New England Journal of Medicine, vol. 344, No. 26, Jun. 28, 2001, pp. 1959-1965.
Ridker et al., "Are Stalins Anti-lnftammatory? Issues in the Design and Conduct of the Pravastatin Inflammation C-Reactive Proetin Evaluation," Current Cardiology Reports, 2000, 2:269-273.
Ridker, "Rapid Reduction in C-Reactive Protein with Cerivastatin Among 785 Patients with Primary Hypercholesterolemia," Circulation, 2001; vol. 103, pp. 1191-1193.
Supplementary Search Report from European Patent Application No. EP02718773.1 dated Feb. 17, 2004.
Schmitt et al., "Leukocytes Utilize Myeloperoxidase-General ed Nitrating Intermediates as Physiological Catalysts for the Generation of Biologically Active Oxidized Lipids and Sterols in Serum," Biochemistry, 1999, vol. 38, pp. 16904-16915.
Supplementary Partial European Search Report from European Patent Application No. EP03724078.5 dated Jun. 13, 2007.
Shishehbor. et al.. "Association of Nitrotyrosine Levels With Cardiovascular Disease and Modulation by Stalin Therapy," JAMA, Apr. 2, 2003, vol. 289, No. 13, pp. 1675-1680.
Steinberg et al., "Beyond Cholesterol: Modifications of Low-Density Lipoprotein that Increase its Atherogenecity," The New England Journal of Medicine, vol. 320, No. 14, Apr. 6, 1989, pp. 915-924.
Stanislaus et al., "Lovastatin Treatment Decreases Mononuclear Cell Infiltration Into the CNS of Lewis Rats with Experimental Allergic Encephalomyelitis," Journal of Neuroscience Research, 66:155-162 (2001).
Strandberg et al., "Associations between change in C-reactive protein and serum lipids during statin treatment," The Finnish Medical Society Duodecim, Ann Med 2000; 32:579-583.
Sugiyama et al., Abstract "Elevated Levels of Plasma Myeloperoxidase, an Oxidative Enzyme Degranulaled from Activated Phagocytes, in Patients with Coronary Artery Disease and Acute Coronary Syndromes," Supplement to Circulation, vol. 106, No. 19, Nov. 5, 2002.
Yasojima et al., "3-Hydroxy-3-methylglutaryl-coenzyme A reductase in mRNA in Alzheimer and control brain," Clinical Neuroscience and Neuropathology, vol. 12, No. 13, Sep. 17, 2001, pp. 2935-2938.
Zhang et al., "Defects in leukocyte-mediated initiation of lipid peroxidalion in plasma as studied in myeloperoxidase-deficient subjects: systematic identification of multiple endogenous diffusible substrates for myeloperoxidase in plasma," Blood, vol. 99, No. 5, pp. 1802-1810.
Zhang et al., "Myeloperoxidase Functions as a Major Enzymatic Catalyst for Initiation of Lipid Peroxidalion at Sites of Inflammation, The Journal of Biological Chemistry," vol. 277, No. 48, Nov. 29, 2002, pp. 46116-46122.
Khan et al., "3-Nitroyrosine in the proteins of human plasma determined by an ELISA method," Biochem J. (1998), 330, pp. 795-801.
International Search Report from International Application No. PCT/US02/00050 dated Jul. 31, 2002.
Hong et al., "Supplemenlaion with Tetrahydrobiopterin Suppress the Development of Hypertension in Spontaneously Hypertension Rats," Hypertension, vol. 38, pp. 1044-1048 (2001).
U.S. Appl. No. 10/972,058, filed Oct. 22, 2004, entitled: Assessing the Risk of a Major Cardiac Event in Patients with Chest Pain.
Jialal, et al., "Low-Density Lipoprotein Oxidation, Antioxidants, and Atherosclerosis, A clinical Biochemistry Perspective," Clinical Chemistry, vol. 42, No. 4, pp. 4980506 (1996).
Beckmann, et al., "Extensive Nitration of Protein Tyrosines in Human Atherosclerosis Detected by Immunohistochemistry," Biol. Chem. Hoppe-Seyler, vol. 375, pp. 81-88, Feb. 1994.
Kooy, et al., Extensive tryosine nitration in human myocardial inftammation:Evidence for the presence of peroxynitrite,: Cir Care Med, vol. 25(5), May 1997; pp. 812.819.
Evans et al., "Do Human Atherosclerotic Lesions Contain Nitrotyrosine?" Biochemical and Biophysical Research Communications, vol. 226, pp. 346-351 (1996).
Supplementary European Search Report from European Patent Application No. 02718773 dated Jan. 29, 2004.
Marquez, et al., "Kinetics of Oxidation of Tyrosine and Dityrosine by Myeloperoxidase Compounds I and 11," The Journal of Biological Chemistry, vol. 270, No. 51, Dec. 22, 1995, pp. 30434-30440.
Abu-Soud, et al., "Nitric Oxide Modulates the Catalytic Activity of Myeloperoxidase," The Journal of Biological Chemistry, vol. 275, No. 8, Feb. 25, 2000, pp. 5425-5430.
Malech, et al., "Primary Inherited Defects in Neutrophil Function: Etiology and Treatment," Seminars in Hematology, vol. 34, No. 4, Oct. 1977, pp. 279-290.

(56) References Cited

OTHER PUBLICATIONS

Heinecke, et al., Mass spectrometric quantification of amino acid oxidation products in proteins: Insights into pathways that promote LDL oxidation in the human artery wall,: FASEB J., vol. 13., pp. 1113-1120 (1999).
Daugherty, et al., "Myeloperoxidase a Catalyst for Lipoprotein Oxidation Is Expressed in Human Atherosclerosis Lesions," J. Clin. Invest., vol. 94, Jul. 1994, pp. 437-444.
Hazen et al.. "3-Chlorotyrosine. a Specific Marker of Myeloperoxidase-catalyzed Oxidation in Markedly Elevated in Low Density Lipoprotein Isolated from Human Atherosclerosis Intima." J. Clin. Invest., vol. 99, No. 9, May 1997, pp. 2075-2081.
Supplementary Partial European Search Report from European Patent Application No. 03724078.5 dated May 31, 2007.
Branchi, et al., "Effects of Low Doses of Simvastatin and Atorvastatin on High-Density Lipoprotein Cholesterol Levels in Patients with Hypercholesterolemia," Clinical Therapeutics, vol. 23, No. 6, 2001, pp. 851.857.
Hazen, et al., "Modification of Proteins and Lipids by Myeloperoxidase," Methods in Enzymology, vol. 300, 1999, pp. 88-105.
Heller, et al., "p-Hydroxpheylacetaldehyde, an Aldehyde Generated by Myeloperoxidase, Modifies Phospholipid Amino Groups of Low Density Lipoprotein in Human Atherosclerosis Intima," The Journal of Biological Chemistry, vol. 275, No. 14, Apr. 7, 2000, pp. 9957-9962.
Madamanchi, N.R., et al., "Oxidative stress in atherogenesis and arterial thrombosis: the disconnect between cellular studies and clinical outcomes," Journal of Thrombosis and Haemostasis, vol. 3, pp. 254-267 (2004).
Zhang. et al., "Association Between Myeloperoxidase Levels and Risk of Coronary Artery Disease," JAMA, Vol, 286, No. 17, Nov. ?, 2001, pp. 2136-2142.
Steinberg, et al., "Is the Oxidative Modification Hypothesis Relevant to Human Artherosclerosis? Do the Antixidant Trials Conducted to Date Refute the Hypothesis?," Circulation, vol. 105, pp. 2107-2111 (2002).
Downs, et al., "Primary Prevention of Acute Coronary Events with Lovastatin in Men and Women with Average Cholesterol Levels," JAMA, vol. 279, No. 20, pp. 1615-1622 (May 27, 1998).
Takemoto, et al., "Pleiotropic Effects of 3-Hydroxy-3-Methylglutaryl Coenzyme A Reductase Inhibitors," Arterioscler Trhom Vase Biol, vol. 21, pp. 1712-1719 (2001).
Vaughan, et al., "The Evolving Role of Stalins in the Management of Artherosclerosis," Journal of the American College of Cardiology, vol. 35, No. 1, pp. 1-10 (2000).
Locatelli, et al. "Reduction of Plasma 24S-Hydroxycholesterol (Cerebrosterol) Levelas Using High-Dosage Simvastatin in Patients with Hypercholesterolemia," Arch Neurology, vol. 59, pp. 213-216, Feb. 2002.
Marx, "Alzeheimer's Disease: Bad for the Heart, Bad for the Mind," Science, vol. 294, pp. 508-509, Oct. 19, 2001.
Heinecke, et al., "Mechanisms of oxidative damage by myeloperoxidase in atherosclerosis and other inflammatory disorders," J. Lab. Clin Med. vol. 133, pp. 321-325, (1999).
Chisolm, et al., The oxidative modification hypothesis of atherogenesis: an overview,: Free Radical Biology & Medicine, vol. 28, No. 12, pp. 815-1826 (2000).
Carr, et al., "Myeloperoxidase binds to low-density lipoprotein:potential implications of atherosclerosis," FEBS Letters, vol. 487, pp. 176-180 (2000).
Baldus, et al., "Myeloperoxidase serum levels predict risk in patients with acute coronary syndromes," Circulation, vol. 108, published on line Sep. 2, 2003, pp. 1440-1445.
Biasucci. et al.. "Intracellular neutrophil myeloperoxidase in reduced in unstable angina and acute myocardial infarction. but its reduction is not related to ischemia." J. Ameri Coll Cardiel, vol. 27, No. 3, pp. 611-616.
Davies, et al., "Thrombosis and Acute Coronary-Artery Lesions in Sudden Cardiac Ischemia Death," N. Engl J. Med., vol. 310, pp. 1138-1140 (1984).
Dinerman, et al.,"Increased Neutrophil Elastase Release in Unstable Angina Pectoris and Acute Myocardial Infarction," J. Am Coll Cardiel, vol. 15, pp. 1559-1563 (1990).
Buffon, et al., "Widespread Coronary lnftammation in Unstable Angina," N. Engl. J Med., vol. 347, pp. 5-12 (2002).
Certified Translation of previously submitted WO 02/50550.
English translation of TERLETSKAYA, Vrach Delo.
"Enzymatic assay of myeloperoxidase" (EC 1.11.1.7) Sigma, revised Jan. 13, 1995, pp. 1-3.
Bergt, Constanze, et al. "Lysine residues direct the chlorination of tyrosines in YXXK motifs of apolipoprotein Al when hypochlorous acid oxidizes high density lipoprotein." Journal of Biological Chemistry 279.9 (2004): 7856-7866.
Brennan, Marie-Luise, et al. "A tale of two controversies defining both the role of peroxidases in nitrotyrosine formation in vivo using eosinophil peroxidase and myeloperoxidase-deficient mice, and the nature of peroxidase-generated reactive nitrogen species." Journal of Biological Chemistry 277.20 (2002): 17415-17427.
Brennan, Marie-Luise, et al. "Prognostic value of myeloperoxidase in patients with chest pain." New England Journal of Medicine 349.17 (2003): 1595-1604.
Cherubini, Antonio, et al. "Antioxidant profile and early outcome in stroke patients." Stroke 31.10 (2000): 2295-2300.
Davi, Giovanni, In vivo formation of 8-Epi-prostaglandin F2beta is increased in Hypercholesterolemia ATVB, 1997: 17:3230-3235, pp. 1-18, atvb.ahajournals.org/contenU 17/1113230.long.
Diaz, Marco N., et al. "Antioxidants and atherosclerotic heart disease." New England Journal of Medicine 337.6 (1997): 408-416.
Faymonville, M. E., et al. "Myeloperoxidase and elastase as markers of leukocyte activation during cardiopulmonary bypass in humans." The Journal of thoracic and cardiovascular surgery 102.2 (1991): 309-317.
Francis, Gordon A., et al. "Oxidative tyrosylation of high density lipoprotein by peroxidase enhances cholesterol removal from cultured fibroblasts and macrophage foam cells." Proceedings of the National Academy of Sciences 90.14 (1993): 6631-6635.
Fu, Shanlin, et al. "Evidence for roles of radicals in protein oxidation in advanced human atherosclerotic plaque." Biochem. J 333 (1998): 519-525.
Gerber et al, Eur. Jour. Clin. Chem. Clin. Biochem., vol. 34, pp. 901-908, 1996.
Davies, Michael J., et al. "Stable markers of oxidant damage to proteins and their application in the study of human disease." Free Radical Biology and Medicine 27.11 (1999): 1151-1163.
Hazen, Stanley L., Fong Fu Hsu, and Jay W. Heinecke. "p-Hydroxyphenylacetaldehyde Is the Major Product of L-Tyrosine Oxidation by Activated Human Phagocytes A chloride-dependent mechanism for the conversion of free amino acids into reactive aldehydes by myeloperoxidase." Journal of Biological Chemistry 271.4 (1996): 1861-1867.
Heinecke, Jay W., et al. "Tyrosyl radical generated by myeloperoxidase catalyzes the oxidative cross-linking of proteins." Journal of Clinical Investigation 91.6 (1993): 2866.
Heinecke, Jay W, "Tyrosyl radical production by myeloperoxidase: a phagocyte pathway for lipid peroxidation and dityrosine cross-linking of proteins." Toxicology 177.1 (2002): 11-22.
Jurst, James K. "Whence nitrotyrosine?." Journal of Clinical Investigation 109.10 (2002): 1287-1290.
Leeuwenburgh, Christiaan, et al. "Mass spectrometric quantification of markers for protein oxidation by tyrosyl radical, copper, and hydroxyl radical in low density lipoprotein isolated from human atherosclerotic plaques." Journal of Biological Chemistry 272.6 (1997): 3520-3526.
Marathe, Gopal K., et al. "Bioactive phospholipid oxidation products." Free Radical Biology and Medicine 28.12 (2000): 1762-1770.
Mehrabi, Mohammad Reza, et al. "The isoprostane, 8-epi-PGF2α, is accumulated in coronary arteries isolated from patients with coronary heart disease." Cardiovascular research 43.2 (1999): 492-499.

(56) References Cited

OTHER PUBLICATIONS

Mohiuddin, Imran, et al. "Nitrotyrosine and chlorotyrosine: clinical significance and biological functions in the vascular system." Journal of Surgical Research 133.2 (2006): 143-149.
Peng, Dao-Quan, et al. "Tyrosine modification is not required for myeloperoxidase-induced loss of apolipoprotein Al functional activities." Journal of Biological Chemistry 280.40 (2005): 33775-33784.
Petibois, Cyril, et al. "Plasma protein contents determined by Fourier-transform infrared spectrometry." Clinical chemistry 47.4 (2001): 730-738.
Hirono, Satoru and Grant N. Pierce, "The Choice of an Appropriate Animal Species in the Study of *Chlamydia pneumoniae* as an Atherogenic Agent." Atherosclerosis, Hypertension and Diabetes. Springer US, 2003. 17-26.
Practico, Domenico, et al. "Vitamin E suppresses isoprostane generation in vivo and reduces atherosclerosis in ApoE-deficient mice." Nature medicine 4.10 (1998): 1189-1192.
Eang, Wen-Qi, et al. "Enhanced cholesterol efflux by tyrosyl radical-oxidized high density lipoprotein is mediated by apolipoprotein Al-All heterodimers." Journal of Biological Chemistry 273.28 (1998): 17391-17398.
Witzum, Joseph L. "To E or not to E—how do we tell?." Circulation 98.25 (1998): 2785-2787.
Zheng, Lemin, et al. "Apolipoprotein Al is a selective target for myeloperoxidase-catalyzed oxidation and functional impairment in subjects with cardiovascular disease." Journal of Clinical Investigation 114.4 (2004): 529.
Zheng, Lemin, et al. "Localization of nitration and chlorination sites on apolipoprotein Al catalyzed by myeloperoxidase in human atheroma and associated oxidative impairment in ABCA1-dependent cholesterol efflux from macrophages." Journal of Biological Chemistry 280.1 (2005): 38-47.

\* cited by examiner

MYELOPEROXIDASE, A RISK INDICATOR FOR CARDIOVASCULAR DISEASE

This application claims priority to U.S. application Ser. No. 14/591,381, filed Jan. 7, 2015, which is a Continuation of U.S. application Ser. No. 11/753,799, filed May 25, 2007, now U.S. Pat. No. 9,170,260, which is a Continuation of U.S. application Ser. No. 10/039,753, filed Jan. 2, 2002, now U.S. Pat. No. 7,223,552, which claims priority to U.S. Provisional Application 60/259,340 filed Jan. 2, 2001 and U.S. Provisional Application 60/283,432 filed May 12, 2001, all of which are incorporated herein in their entirety.

The work described in this application was supported, at least in part, by Grant No. RO1 HL62526-01 from the National Institutes of Health. The United States government has certain rights in this invention.

BACKGROUND

The present invention relates to the field of cardiovascular disease. More specifically, it relates to a diagnostic test which can be used to determine whether an individual or test subject is at a lower risk or higher risk of developing or having cardiovascular disease than other individuals in a given population of human subjects.

Cardiovascular disease (CVD) is the general term for heart and blood vessel diseases, including atherosclerosis, coronary heart disease, cerebrovascular disease, and peripheral vascular disease. Cardiovascular disorders are acute manifestations of CVD and include myocardial infarction, stroke, angina pectoris, transient ischemic attacks, and congestive heart failure. CVD accounts for one in every two deaths in the United States and is the number one killer disease. Thus, prevention of cardiovascular disease is an area of major public health importance.

A low fat diet and exercise are recommended to prevent CVD. In addition, a number of drugs may be prescribed by medical professionals to those persons who are known to be at risk for developing CVD. These include lipid lowering agents which reduce blood levels of cholesterol and trigylcerides. Medications to normalize blood pressure are used in hypertensive patients. Medications which prevent activation of platelets, such as aspirin, may also be prescribed for patients at risk for developing CVD. More aggressive therapy, such as administration of multiple medications, may be used in those individuals who are at high risk. Since CVD therapies may have adverse side effects, it is desirable to have diagnostic tests for identifying those individuals who are at risk, particularly those individuals who are at high risk, of developing CVD.

Currently, several risk factors are used by members of the medical profession to assess an individual's risk of developing CVD and to identify individuals at high risk. Major risk factors for cardiovascular disease include hypertension, family history of premature CVD, smoking, high total cholesterol, low HDL cholesterol, and diabetes. The major risk factors for CVD are additive, and are typically used together by physicians in a risk prediction algorithm to target those individuals who are most likely to benefit from treatment for CVD. These algorithms achieve a high sensitivity and specificity for predicting 15% risk of CVD within 10 years. However, the ability of the present algorithms to predict a higher probability of developing CVD is limited. Among those individuals with none of the current risk factors, the 10-year risk for developing CVD is still about 2%. In addition, a large number of cardiovascular disorders occur in individuals with apparently low to moderate risk profiles, as determined using currently known risk factors. Thus, there is a need to expand the present cardiovascular risk algorithm to identify a larger spectrum of individuals at risk for or affected with CVD.

The mechanism of atherosclerosis is not well understood. Over the past decade a wealth of clinical, pathological, biochemical and genetic data support the notion that atherosclerosis is a chronic inflammatory disorder. Acute phase reactants (e.g. C-reactive protein, complement proteins), sensitive but non-specific markers of inflammation, are enriched in fatty streaks and later stages of atherosclerotic lesions. In a recent prospective clinical trial, base-line plasma levels of C-reactive protein independently predicted risk of first-time myocardial infarction and stroke in apparently healthy individuals. U.S. Pat. No. 6,040,147 describes methods which use C-reactive protein, cytokines, and cellular adhesion molecules to characterize an individual's risk of developing a cardiovascular disorder. Although useful, these markers may be found in the blood of individuals with inflammation due to causes other than CVD, and thus, these markers are not highly specific.

Accordingly, the need still exits for additional diagnostic tests for characterizing an individuals risk of developing or of having cardiovascular disease. Diagnostic tests which employ risk factors that are independent of traditional CVD risk factors such as LDL levels are especially desirable.

SUMMARY OF THE INVENTION

The present invention provides new diagnostic tests for characterizing an individual's risk of developing or having cardiovascular disease. The present tests are especially useful for identifying those individuals who are in need of highly aggressive CVD therapies as well as those individuals who require no therapies targeted at preventing CVD. The present diagnostic tests are based on the discovery that patients with coronary artery disease (CAD) have significantly greater levels of leukocyte and blood myeloperoxidase (MPO) levels than patients without angiographically significant CAD. It has also been discovered that leukocyte-MPO levels in CAD and non-CAD patients are independent of age, sex, diabetes, hypertension, smoking (ever or current), WBC count, LDL-C, trigylcerides, and Framingham Global Risk Score. Thus, the present diagnostic tests, which involve assessing levels of MPO activity, MPO mass, or levels of select MPO-generated oxidation products in a blood sample or derivative thereof from a test subject, provide additive predictive value beyond that seen with clinical and diagnostic risk factors currently employed by physicians.

In one aspect, the present diagnostic test comprises determining the level of MPO activity in a bodily sample obtained from the individual or test subject. The bodily sample is blood or a derivative thereof, including but not limited to, leukocytes, neutrophils, monocytes, serum, or plasma. The level of MPO activity in the bodily sample from the test subject is then compared to a predetermined value that is derived from measurements of MPO activity in comparable bodily samples obtained from the general population or a select population of human subjects. Such comparison characterizes the test subject's risk of developing CVD. For example, test subjects whose blood levels of MPO activity are higher than the predetermined value are at greater risk of developing or having CVD than individuals whose blood MPO activity levels are at or lower than the predetermined value. Moreover, the extent of the difference between the test subjects MPO activity levels and predetermined value is also useful for characterizing the extent of the risk and thereby, determining which individuals would most greatly benefit from certain therapies.

In another aspect, the diagnostic test comprises determining the level of MPO mass in a bodily sample obtained from the test subject. The bodily sample is blood or a derivative thereof, including but not limited to, leukocytes, neutrophils, monocytes, serum, or plasma. Levels of MPO mass in bodily samples from the test subject are then compared to a predetermined value that is derived from measurements of MPO mass in comparable bodily samples obtained from healthy controls. Such comparison characterizes the test subject's risk of developing CVD.

In another aspect, the diagnostic test comprises determining the level of one or more select MPO-generated oxidation products in a bodily sample obtained from the test subject. The select MPO-generated oxidation products are dityrosine, nitrotyrosine, methionine sulphoxide, and MPO-generated lipid peroxidation products. Preferred MPO lipid peroxidation products are hydroxy-eicosatetraenoic acids (HETEs); hydroxy-octadecadienoic acids (HODEs); F2Isoprostanes; the glutaric and nonanedioic monoesters of 2-lysoPC (G-PC and ND-PC, respectively); the 9-hydroxy-10-dodecenedioic acid and 5-hydroxy-8-oxo-6-octenedioic acid esters of 2-lysoPC (HDdiA-PC and HOdiA-PC, respectively); the 9-hydroxy-12-oxo-10-dodecenoic acid and 5-hydroxy-8-oxo-6-octenoic acid esters of 2-lysoPC (HODA-PC and HOOA-PC, respectively); the 9-keto-12-oxo-10-dodecenoic acid and 5-keto-8-oxo-6-octenoic acid esters of 2-lysoPC (KODA-PC and KOOA-PC, respectively); the 9-keto-10-dodecendioic acid and 5-keto-6-octendioic acid esters of 2-lysoPC (KDdiA-PC and KOdiA-PC, respectively); the 5-oxovaleric acid and 9-oxononanoic acid esters of 2-lysoPC (OV-PC and ON-PC, respectively); 5-cholesten-5α,6α-epoxy-3β-ol (cholesterol α-epoxide); 5-cholesten-5β,6β-epoxy-3β-ol (cholesterol β-epoxide); 5-cholesten-3β,7β-diol (7-OH-cholesterol); 5-cholesten-3β, 25-diol (25-OH cholesterol); 5-cholesten-3β-ol-7β-hydroperoxide (7-OOH cholesterol); and cholestan-3β,5α6β-triol (triol). The bodily sample is blood, urine or a blood derivative, including but not limited to, leukocytes, neutrophils, monocytes, serum, or plasma. Levels of the selected MPO-generated oxidation products in bodily samples from the test subject are then compared to a predetermined value that is derived from measurements of the selected MPO-generated oxidation products in comparable bodily samples obtained from healthy controls. Such comparison characterizes the test subject's risk of developing CVD.

For those individuals who have already experienced an acute adverse cardiovascular event such as a myocardial infarction or ischemic stroke, the present diagnostic tests are also useful for assessing such individual's risk of having a recurrent event. Thus, the present invention also provides a method for monitoring over time the status of CVD in a subject. The method comprises determining the levels of one or more of the present risk factors, including MPO activity, MPO mass, select MPO-generated oxidation products, and combinations thereof, in a bodily sample taken from the subject at an initial time and in a corresponding bodily fluid taken from the subject at a subsequent time. An increase in the levels of the present risk factors from the bodily fluid taken at the subsequent time as compared to the initial time indicates that a subject's risk of having a future cardiovascular event/disorder has increased. A decrease in the levels of the present risk factors from the bodily fluid taken at the subsequent time as compared to the initial time indicates that that the subject's risk of having a cardiovascular event has decreased.

In another aspect, the present invention provides a method for evaluating therapy in a subject suspected of having or having cardiovascular disease. The method comprises determining the levels of one or more of the present risk factors, including MPO activity, MPO mass, select MPO-generated oxidation products, and combinations thereof, in a bodily sample taken from the subject prior to therapy and a corresponding bodily fluid taken from the subject during or following therapy. A decrease in the level of the selected risk factor in the sample taken after or during therapy as compared to the level of the selected risk factor in the sample taken before therapy is indicative of a positive effect of the therapy on cardiovascular disease in the treated subject.

DETAILED DESCRIPTION OF THE INVENTION

Figure 1:
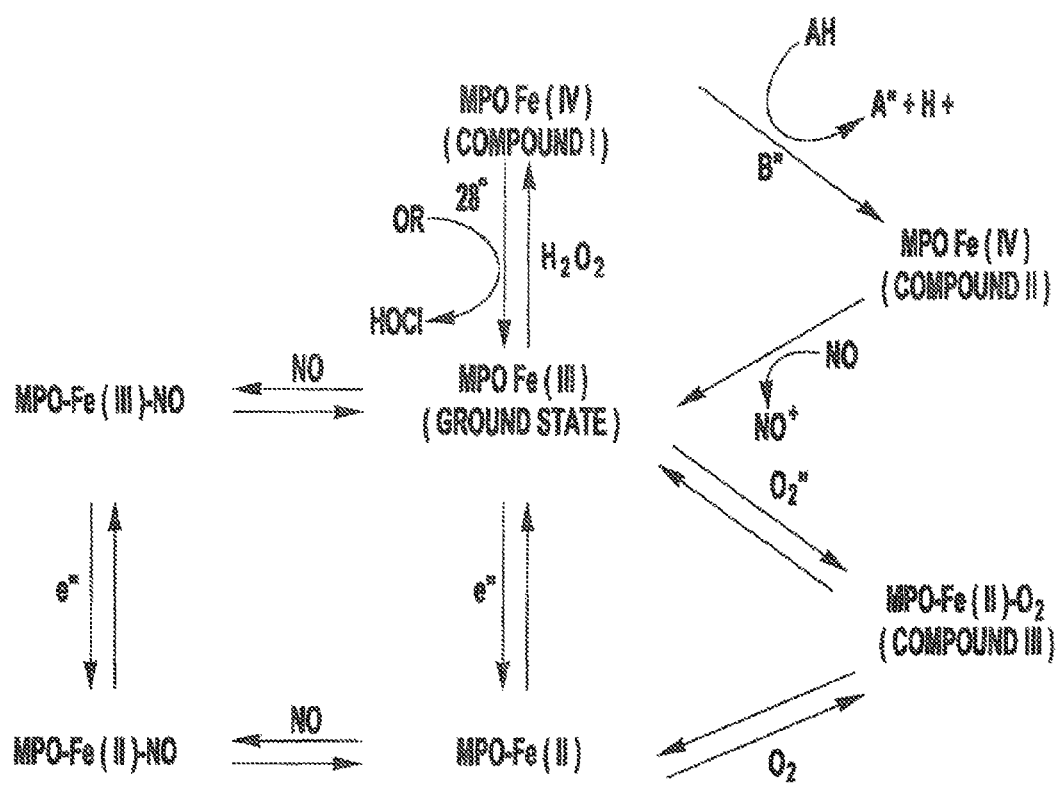
FIG. 1. A kinetic model for myeloperoxidase.

All references cited herein are specifically incorporated herein by reference.

The present invention provides diagnostic tests for characterizing an individual's risk for developing or having CVD. In one aspect, the method comprises obtaining the level of MPO activity in a bodily sample obtained from the individual. In another aspect, the method comprises obtaining the level of MPO mass in a bodily sample from the individual. In another aspect, the method comprises obtaining the level of one or more select MPO-generated oxidation products in a bodily sample from the individual or test subject. Such MPO-generated oxidation products are selected from the group consisting of dityrosine, nitrotyrosine, methionine sulphoxide and a lipid peroxidation product. In yet another aspect, the method comprises obtaining the level of MPO activity, or MPO mass, or both and the level of one or more select MPO-generated oxidation products in a bodily sample obtained from the individual.

The level of MPO activity or MPO mass or select MPO-generated oxidation product in the individual's bodily sample is then compared to a predetermined value to provide a risk value which characterizes the individual's risk of developing or having CVD.

The present invention also relates to kits that comprise assays for MPO activity or mass, or the select MPO-generated oxidation product. Such assays have appropriate sensitivity with respect to predetermined values selected on the basis of the present diagnostic tests. The present kits differ from those presently commercially available for MPO by including, for example, different cut-offs, different sensitivities at particular cut-offs, as well as instructions or other printed material for characterizing risk based upon the outcome of the assay.

Preparation of Bodily Sample

Whole blood is obtained from the individual or test subject using standard clinical procedures. Plasma is obtained from whole blood samples by centrifugation of anti-coagulated blood. Such process provides a buffy coat of white cell components and a supernatant of the plasma.

Serum is collected by centrifugation of whole blood samples that have been collected in tubes that are free of anti-coagulant. The blood is permitted to clot prior to centrifugation. The yellowish-reddish fluid that is obtained by centrifugation is the serum.

Leukocytes can be isolated from whole blood samples by any of various techniques including buoyant density centrifugation as described in the examples below.

Myeloperoxidase and Myeloperoxidase-Generated Oxidation Products

MPO (donor: hydrogen peroxide, oxidoreductase, EC 1.11.1.7) is a tetrameric, heavily glycosylated, basic (Pl. 10) heme protein of approximately 150 kDa. It is comprised of two identical disulfide-linked protomers, each of which possesses a protoporphyrin-containing 59-64 kDa heavy subunit and a 14 kDa light subunit (Nauseef, W. M, et al., *Blood* 67:1504-1507; 1986.)

MPO is abundant in neutrophils and monocytes, accounting for 5%, and 1 to 2%, respectively, of the dry weight of these cells (Nauseef, W. M, et al., *Blood* 67:1504-1507; 1986., (Hurst, J. K. In: Everse J.; Everse K.; Grisham M. B., eds. Peroxidases in chemistry and biology 1st ed. Boca Raton: CRC Press; 1991:37-62.) The heme protein is stored in primary azurophilic granules of leukocytes and secreted into both the extracellular milieu and the phagylysosomal compartment following phagocyte activation by a variety of agonists (Klebanoff, S. J, et al. *The neutrophil: functions and clinical disorders*. Amsterdam: Elsevier Scientific Publishing Co.; 1978.) Immunohistochemical methods have demonstrated that MPO is present in human atherosclerotic lesions. However, MPO has not yet been shown to be present at increased levels in blood samples from individuals with atherosclerosis.

A recently proposed working kinetic model for MPO is shown in FIG. 1. MPO is a complex heme protein which possesses multiple intermediate states, each of which are influenced by the availability of reduced oxygen species such as $O_2^-$ and $H_2O_2$, and nitric oxide (NO, nitrogen monoxide) (Abu-Soud, H. M., et al., *J. Biol. Chem.* 275: 5425-5430; 2000). At ground state, MPO exists in the ferric (Fe(III)) form. Upon addition of $H_2O_2$, the heme group of MPO is oxidized two $e^-$ equivalents forming a reactive ferryl π cation radical intermediate termed Compound I. In the presence of halides such as $Cl^-$, $Br^-$, and $I^-$, and the psuedohalide thiocyanate ($SCN^-$), Compound I is readily reduced in a single two $e^-$ step, regenerating MPO-Fe(III) and the corresponding hypohalous acid (HOX). At plasma levels of halides and thiocyanate (100 mM $Cl^-$, 100 mM $Br^-$ 50 mM SCN, 100 nM $I^-$, chloride is a preferred substrate and hypochlorous acid (HOCl), a potent chlorinating oxidant, is formed (Foote, C. S., et al; *Nature* 301:715-726; 1983., Weiss, S. J., et al. *J. Clin. Invest.* 70:598-607; 1982).

Compound I can also oxidize numerous organic substrates while the heme undergoes two sequential one $e^-$ reduction steps, generating compound II and MPO-Fe(III), respectively (FIG. 1). Low molecular weight compounds primarily serve as substrates for MPO, generating diffusible oxidants and free radical species which can then convey the oxidizing potential of the heme to distant targets. In addition to halides and $SCN^-$, some of the naturally occurring substrates for MPO include nitrite ($NO_2^-$) (van der Vliet, A., et al., *J. Biol. Chem.* 272:7617-7625; 1997), tyrosine (van der Vliet, A., et al., *J. Biol. Chem.* 272:7617-7625; 1997), ascorbate (Marquez, L. A., et al., *J. Biol. Chem.* 265:5666-5670; 1990), urate (Maehly, H. C. *Methods Enzymol.* 2:798-801; 1955), catecholamines (Metodiewa, D., et al, *Eur. J. Biochem.* 193:445-448; 1990), estrogens (Klebanoff, S. *J. J. Exp. Med* 145:983-998; 1977), and serotonin (Svensson, B. E. *Chem. Biol. Interact.* 70:305-321; 1989). MPO-Fe(III) can also be reduced to an inactive ferrous form, MPO-Fe(II) (Hurst, J. K. In: Everse J.; Everse K.; Grisham M. B., eds. Peroxidases in chemistry and biology 1st ed. Boca Raton: CRC Press; 1991:37-62., (Kettle, A. J., et al., *Redox. Rep.* 3:3-15; 1997). MPO-Fe(III) and MPO-Fe(II) bind to $O_2^-$, and $O_2$, respectively, forming a ferrous dioxy intermediate, compound III (MPO-Fe(II)-$O_2$) (FIG. 1). Spectral studies demonstrate that addition of $H_2O_2$ to Compound III ultimately forms compound II. Thus, compound III may indirectly promote one $e^-$ peroxidation reactions.

Recent studies identify a role for NO, a relatively long-lived free radical generated by nitric oxide synthase (NOS), in modulating MPO peroxidase activity (Abu-Soud, H. M., et al., *J. Biol. Chem.* 275:5425-5430; 2000). MPO and the inducible isoform of NOS are colocalized in the primary granule of leukocytes. During phagocyte activation, such as during ingestion of bacteria, MPO and NOS are secreted into the phagolysosome and extracellular compartments, and nitration of bacterial proteins is observed (Evans, T. J., et al., *Proc. Natl. Acad. Sci. USA* 93:9553-9558; 1996). Rapid kinetics studies demonstrate that at low levels of NO, the initial rate of MPO-catalyzed peroxidation of substrates is enhanced. The mechanism is through acceleration of the rate-limiting step in MPO catalysis, reduction of compound I to MPO-Fe(III) (FIG. 1) (Abu-Soud, H. M., et al., *J. Biol. Chem.* 275:5425-5430; 2000., Abu-Soud, H. M., et al. Nitric oxide is a physiological substrate for mammalian animal peroxidases. Submitted; 2000). At higher levels of NO, reversible inhibition of MPO occurs through formation of a spectroscopically distinguishable nitrosyl complex, MPO-Fe(III)-NO (Abu-Soud, H. M., et al., *J. Biol. Chem.* 275: 5425-5430; 2000). NO also can serve as a substrate for MPO compound I, resulting in its reduction to Compound II (Abu-Soud, H. M., et al. Nitric oxide is a physiological substrate for mammalian animal peroxidases. Submitted; 2000). Furthermore, in the presence of NO, the overall turnover rate of MPO through the peroxidase cycle is enhanced nearly 1000-fold (Abu-Soud, H. M., et al. Nitric oxide is a physiological substrate for mammalian animal peroxidases. Submitted; 2000). Finally, NO also reversibly binds to MPO-Fe(II) forming the corresponding MPO-Fe (II)-NO intermediate, which is in equilibrium with MPO-Fe(II) and MPO-Fe(III)-NO (FIG. 1) (Abu-Soud, H. M., et al., *J. Biol. Chem.* 275:5425-5430; 2000., Abu-Soud, H. M., et al. Nitric oxide is a physiological substrate for mammalian animal peroxidases. Submitted; 2000).

Figure 2:
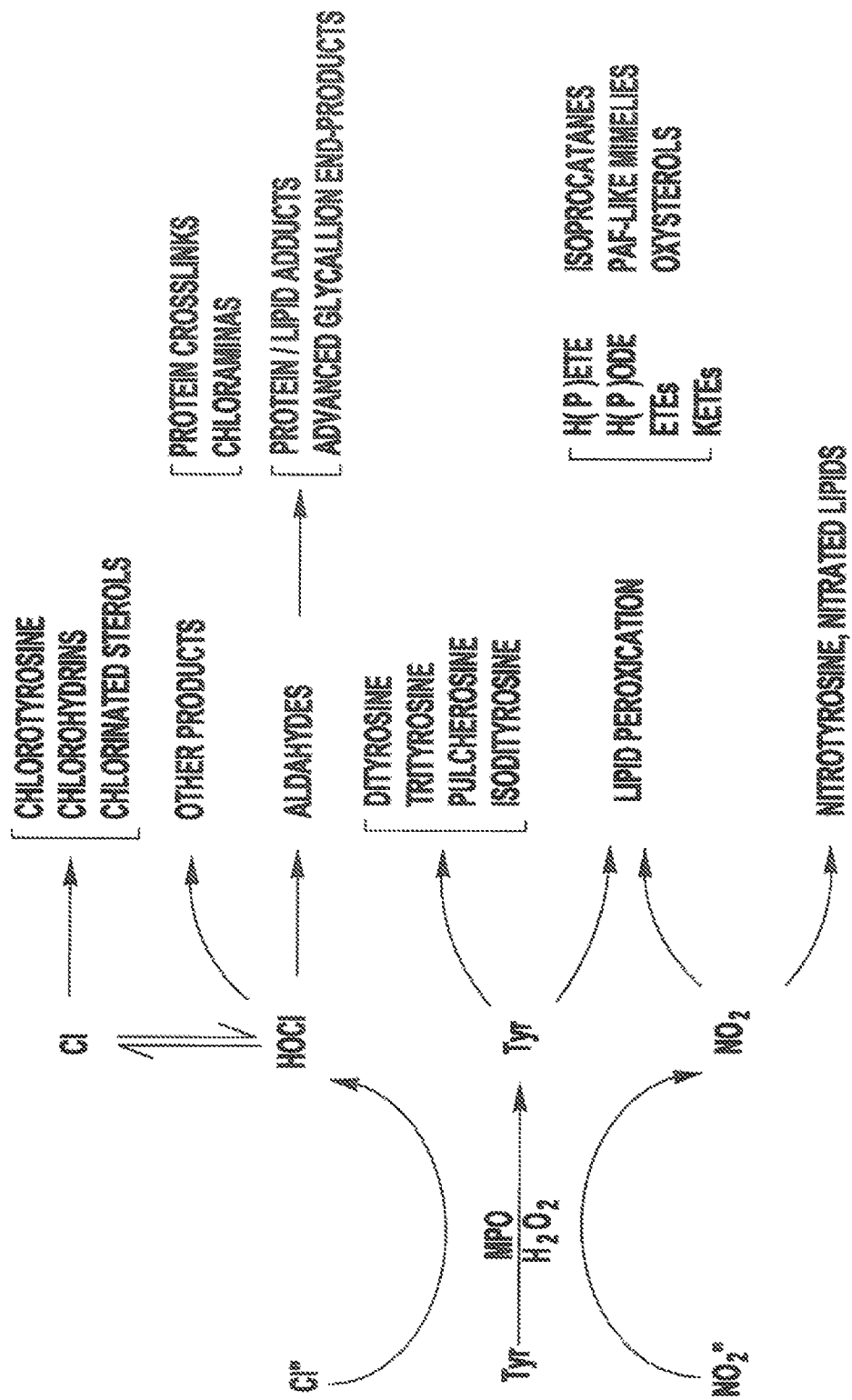
FIG. 2. A schematic representation of certain myeloperoxidase generated reactive intermediates and some MPO-generated oxidation products.

As described above, MPO can utilize a variety of cosubstrates with $H_2O_2$ to generate reactive oxidants as intermediates. Many stable end-products generated by these species have been characterized and shown to be enriched in proteins, lipids, and LDL recovered from human atherosclerotic lesions (Chisolm, G. M., et al., *Proc. Natl. Acad. Sci. USA* 91:11452-11456; 1994, Hazell, L. J., et al, *J. Clin. Invest.* 97:1535-1544; 1996, Hazen, S. L., et al., *J. Clin. Invest.* 99:2075-2081; 1997, Leeuwenburgh, C., et al, *J. Biol. Chem.* 272:1433-1436; 1997, Leeuwenburgh, C., et al., *J. Biol. Chem.* 272:3520-3526; 1997). FIG. 2 summarizes some of the reactive intermediates and products formed by MPO, any of which are known to be enriched in vascular lesions.

Methods of Determining MPO Activity

Myeloperoxidase activity may be determined by any of a variety of standard methods known in the art. One such method is a colorimetric-based assay where a chromophore that serves as a substrate for the peroxidase generates a product with a characteristic wavelength which may be followed by any of various spectroscopic methods including UV-visible or fluorescence detection. Additional details of colorimetric based assays can be found in Kettle, A. J. and Winterboum, C. C. (1994) *Methods in Enzymology.* 233: 502-512; and Klebanoff, S. J., Waltersdorph, A. N. and Rosen, H. (1984) *Methods in Enzymology.* 105: 399-403, both of which are incorporated herein by reference. An article by Gerber, Claudia, E. et al, entitled "Phagocytic Activity and Oxidative Burst of Granulocytes in Persons with Myeloperoxidase Deficiency" published in 1996 in Eur. J. Clin. Chem Clin Biochem 34:901-908, describes a method for isolation for polymorphonuclear leukocytes (i.e. neutrophils) and measurement of myeloperoxidase activity with a colorometric assay, which involves oxidation of the chromogen 4-chloro-1-naphthol.

Peroxidase activity may be determined by in situ peroxidase staining in MPO containing cells with flow cytomeny-based methods. Such methods allow for high through-put screening for peroxidase activity determinations in leukocytes and subpopulations of leukocytes. An example is the cytochemical peroxidase staining used for generating white blood cell count and differentials with hematology analyzers based upon peroxidase staining methods. For example, the Advia 120 hematology system by Bayer analyzes whole blood by flow cytometry and performs peroxidase staining of white blood cells to obtain a total white blood cell count (CBC) and to differentiate amongst the various white blood cell groups.

With these methods, whole blood enters the instrument and red blood cells are lysed in a lysis chamber. The remaining white blood cells are then fixed and stained in situ for peroxidase activity. The stained cells are channeled into the flow cytometer for characterization based upon the intensity of peroxidase staining and the overall size of the cell, which is reflected in the amount of light scatter of a given cell. These two parameters are plotted on the x and y axis, respectively, by conventional flow cytometry software, and clusters of individual cell populations are readily discernible. These include, but are not limited, to neutrophils, monocytes and eosinophils, the three major leukocyte populations containing visible peroxidase staining.

During the course of these analyses, leukocytes such as monocytes, neutrophils, eosinophils and lymphocytes are identified by the intensity of peroxidase staining and their overall size. Information about the overall peroxidase activity staining within specific cell populations is thus inherent in the position of individual cell clusters (e.g. neutrophil, monocyte, eosinophil clusters) and peroxidase levels within specific cell populations may be determined. Peroxidase activity/staining in this detection method is compared to a peroxidase stain reference or calibrant. Individuals with higher levels of peroxidase activity per leukocyte are identified by having a cell population whose location on the cytogram indicates higher levels of peroxidase (i.e., average peroxidase activity per leukocyte) or by demonstrating a sub-population of cells within a cell cluster (e.g. neutrophil, monocyte, eosinophil clusters) which contain higher levels of peroxidase activity either on average or in a higher subgroup, such as the higher tertile or quartile.

Methods of Determining MPO Mass

The mass of myeloperoxidase in a given sample is readily determined by an immunological method, e.g. ELISA. Commercial kits for MPO quantification by ELISA are available.

MPO mass in a sample can also be determined indirectly by in situ peroxidase staining of the bodily sample. Methods which analyze leukocyte peroxidase staining can be performed on whole blood, such as those with hematology analyzers which function based upon in situ peroxidase staining. Previous studies by other investigators have demonstrated that the overall intensity of staining is proportional to peroxidase mass (e.g. Claudia E. Gerber, Selim Kuci, Matthias Zipfel, Ditrich Niethammer and Gernot Bruchfelt, "Phagocytic activity and phagocytic activity and oxidative burst of granulocytes in persons with myeloperoxidase deficiency" European Journal of Clinical Chemistry and Clinic Biochemistry (1996) 34: 901-908).

Flow cytometry through a hematology analyzer is a high through-put technique for quantifying the parameters used in determining MPO activity or mass levels or numbers of cells containing elevated levels of MPO activity or mass. The advantage of using such a technique is its ease of use and speed. The Advia 120 can perform 120 complete cell blood count and differentials in one hour and utilizes only a few microliters of blood at a time. All the data necessary for determination of the peroxidase activity is held within the flow cytometry cell clusters used to ultimately calculate the total white blood cell count and differential. With minor adjustments to software of this apparatus, the readout can be modified to include multiple different indices of overall peroxidase activity. For example, individuals whose neutrophil clusters contain an overall increase in the average peroxidase activity (i.e. increased mean peroxidase index) will be at increased risk for development of cardiovascular disease. In addition to simply determining the mean peroxidase activity for a given cell type, individuals at increased risk of developing CVD can be identified by examining the overall distribution of peroxidase activity within a given cell cluster (mean+mode, etc). It is expected that by looking at the population of peroxidase activity per leukocyte, individuals who possess leukocytes with a higher proportion of cells containing a high peroxidase activity in a subset of cells (for example, the upper quartile, or the upper tertile) may be at particularly high risk.

Levels of MPO Activity and MPO Mass

The level of MPO activity or MPO mass in the body fluid can be determined by measuring the MPO activity or MPO mass in the body fluid and normalizing this value to obtain the MPO activity or mass per ml of blood, per ml of serum, per ml of plasma, per leukocyte (e.g. neutrophil or monocyte), per weight, e.g. mg of total blood protein, per weight of leukocyte protein (e.g. per weight of neutrophil or monocyte protein). Alternatively, the level of MPO activity or MPO mass in the body fluid can be a representative value which is based on MPO activity in the test subjects blood or blood derivatives. For example the level of MPO activity can be the percentage or the actual number of the test subject's neutrophils or monocytes that contain elevated levels of MPO activity or MPO mass. Examples of other representative values include, but are not limited to, arbitrary units for a parameter that can be obtained from a flow cytometry based cytogram, such as the position of the neutrophil cluster on the X and Y axes, or the angle of the major axis of the neutrophil cluster relative to the X and Y axes.

Myeloperoxidase-Generated Oxidation Products

Role of MPO in the Generation of HETEs and HODEs and Oxidized Cholesterol Esters A role for MPO in the oxidation of LDL and the initiation of lipid peroxidation has recently been questioned by several investigators. Noguchi and colleagues examined the capacity of leukocytes isolated from wild-type and MPO knockout mice to promote oxidation of LDL in model systems ex vivo and observed only modest differences in the parameters of lipid oxidation monitored. (Noguchi N, et al. J. Biochem. (Tokyo) 2000; 127:971-976). It has also recently been suggested that MPO-catalyzed oxidation of LDL is inhibited, rather than promoted, by the presence of $NO_2^-$, particularly when focusing upon protein oxidation products. (Carr A C, et al, J. Biol. Chem. 2001; 276:1822-1828). Moreover, an antioxidant rather than a pro-oxidant function for MPO-generated tyrosine oxidation products and LDL oxidation has been proposed. (Santanam N., et al. J. Clin. Invest 1995; 95:2594-2600, Exner M. et al., FEBS Lett. 2001; 490:28-31). It has also been suggested by some investigators that HOCl generated by MPO can promote oxidation of lipoprotein lipids and formation of hydroperoxides (Panasenko O M., Biofactors 1997; 6:181-190), whereas other studies have not supported these observations. (Schmitt D, et al., Biochem. 1999; 38:16904-16915, Hazen S L, et al., Circ. Res. 1999; 85:950-958). Finally, recent studies have noted species differences between murine and human leukocytes with respect to MPO and generation of reactive oxidant species. (Xie Q W, et al., Biological oxidants: generation and injurious consequences. San Diego, Calif., USA, Academic Press, 1992, Rausch P G, et al., Blood 1975; 46:913-919, Nauseef W M., J. Clin. Invest 2001; 107:401-403, Brennan M L, et al. J. Clin. Invest 2001; 107:419-430).

To determine the role of MPO in promoting lipid oxidation in plasma, we incubated activated neutrophils from healthy subjects and subjects with a myeloperoxidase deficiency with whole plasma (50%, v/v) and physiological levels of Cl⁻ (100 mM final). Phagocytes were activated with PMA and the formation of specific oxidation products of linoleic and arachidonic acids, respectively, was determined by LC/ESI/MS/MS.

MPO and Lipoprotein Isolation

MPO (donor: hydrogen peroxide, oxidoreductase, EC 1.11.1.7) was isolated and characterized as described. (Heinecke J W, et al., J. Biol. Chem. 1993; 268:4069-4077, Wu W, et al., Biochemistry 1999; 38:3538-3548). Purity of isolated MPO was established by demonstrating a R/Z≥0.85 ($A_{430}/A_{280}$), SDS PAGE analysis with Coomassie Blue staining, and in-gel tetramethylbenzidine peroxidase staining to confirm no eosinophil peroxidase contamination. (Wu W, et al., Biochemistry 1999; 38:3538-3548). Purified MPO was stored in 50% glycerol at −20° C. Enzyme concentration was determined spectrophotometrically ($\epsilon_{430}$=170,000 $M^{-1}cm^{-1}$). (Odajima T, et al. Biochim. Biophys. Acta. 1970; 71-77). LDL was isolated from fresh plasma by sequential ultracentrifugation as a 1.019<d<1.063 g/ml fraction with dialysis performed in sealed jars under argon atmosphere. (Hatch F T. Adv. Lipid Res. 1968; 6:1-68). Final preparations were kept in 50 mM sodium phosphate (pH 7.0), 100 μM DTPA and stored under $N_2$ until use. LDL concentrations are expressed per mg of LDL protein.

Human Neutrophil Preparations

Human neutrophils were isolated from whole blood obtained from normal and MPO-deficient subjects, as described. (Hazen S L, et al., J. Biol. Chem. 1996; 271: 1861-1867). Neutrophils preparations were suspended in HBSS ($Mg^{2+}$—, $Ca^{2+}$—, phenol- and bicarbonate-free, pH 7.0) and used immediately for experiments.

Lipid Peroxidation Reaction

Isolated human neutrophils ($10^6$/ml) were incubated at 37° C. with either 50% (v/v) normal human plasma or isolated human LDL (0.2 mg/ml) under air in HBSS supplemented with 100 μM DTPA. Neutrophils were activated by adding 200 nM phorbol myristate acetate (PMA) and maintained in suspension by gentle mixing every 5 min. After 2 h, reactions were stopped by immersion in ice/water bath, centrifugation at 4° C. and immediate addition of 50 μM butylated hydroxytoluene (BHT) and 300 nM catalase to the supernatant. Lipid peroxidation products in the supernatant were then rapidly assayed as described below.

Reactions with isolated MPO were typically performed at 37° C. in sodium phosphate buffer (20 mM, pH 7.0) supplemented with 100 μM DTPA using 30 nM MPO, 1 mM glucose (G), 20 ng/ml glucose oxidase (GO). Under this condition, a constant flux of $H_2O_2$ (0.18 μM/min) was generated by the glucose/glucose oxidase (G/GO) system. Unless otherwise stated, reactions were terminated by immersion in ice/water bath and addition of both 50 μM BHT and 300 nM catalase to the reaction mixture.

Lipid Extraction and Sample Preparation

Lipids were extracted and prepared for mass spectrometry analysis under argon or nitrogen atmosphere at all steps. First, hydroperoxides in the reaction mixture were reduced to their corresponding hydroxides by adding $SnCl_2$ (1 mM final). A known amount of deuterated internal standard, 12(S)-hydroxy-5,8,10,14-eicosatetraenoic-5,6,8,9,11,12,14, 15-d8 acid (12-HETE-d8; Cayman Chemical Company, Ann Arbor, Mich.) was added to the sample, and then plasma lipids were extracted by adding a mixture of 1 M acetic acid/2-isopropanol/hexane (2/20/30, v/v/v) at a ratio of 5 ml organic solvent mix: 1 ml plasma. Following vortexing of the mixture and centrifugation, lipids were extracted into the hexane layer. Plasma was re-extracted by addition of an equal volume of hexane, followed by vortexing and centrifugation. Cholesteryl ester hydroperoxides (CE-H(P) ODEs) were analyzed as their stable $SnCl_2$-reduced hydroxide forms by drying the combined hexane extracts under $N_2$, reconstituting samples with 200 μl 2-isopropanol/acetonitrile/water (44/54/2, v/v/v) and storage at −80° C. under argon until analysis. For the assay of free fatty acids and their oxidation products, total lipids (phospholipids, cholesterol esters, triglycerides) were dried under $N_2$, re-suspended in 1.5 ml 2-isopropanol and then fatty acids were released by base hydrolysis with 1.5 ml 1M NaOH at 60° C. for 30 min under argon. The hydrolyzed samples were acidified to pH 3.0 with 2M HCl and fatty acids were extracted twice with 5 ml hexane. The combined hexane layers were dried under $N_2$, resuspended in 100 μl methanol and stored under argon at −80° C. until analysis by LC/ESI/MS/MS), as described below.

HPLC Fractionation of Plasma Filtrate

In order to study the role played by low molecular weight compounds in plasma as substrates for MPO in promotion of lipid peroxidation, whole plasma from normal healthy donors was filtered through a 10 kDa MWt cut off filter (Centriprep YM-10, Millipore-Corporation Bedford, Mass. USA) by centrifugation. The filtrate of plasma was used either directly or following fractionation by HPLC. Reverse phase HPLC fractionation of was performed using a Beckman C-18 column (4.6×250 mm, 5 μm ODS; Beckman Instruments, Inc. Fullerton, Calif.). The separation of low molecular weight compounds in plasma filtrate (0.5 ml) was carried out at the flow rate 1.0 ml/min with the following gradient: 100% mobile phase A (water containing 0.1% acetic acid) over 10 min, then linear gradient to 100% mobile phase B (methanol containing 0.1% acetic acid) over 10 min, followed by 100% mobile phase B over 5 min. Effluent was collected as 1 ml fractions, dried under $N_2$, and then resuspended in buffer (0.1 ml) for analysis. Fractionation of plasma filtrate (0.5 ml) by strong anion exchange HPLC (SAX-HPLC) was performed on a SPHERIS HPLC column (4.6×250 mm, 5 μm SAX; Phase Separations Inc. Norwalk Conn.). The separation of low molecular weight compounds in plasma filtrate was carried out at the flow rate 0.9 ml/min under isocratic conditions using 45 mM ammonium acetate buffer (pH 4.0) as mobile phase. Effluent was collected as 1.0 ml fractions, dried under $N_2$, and then resuspended in buffer (0.1 ml) for analysis.

a) Mass Spectrometry

LC/ESI/MS/MS was employed to quantify free radical-dependent oxidation products of arachidonic acid (9-hydroxy-5,7,11,14-eicosatetraenoic acid and 9-hydroperoxy-5, 7,11,14-eicosatetraenoic acid (9-H(P)ETE)), and linoleic acid (9-hydroxy-10,12-octadecadienoic acid and 9-hydroperoxy-10,12-octadecadienoic acid (9-H(P)ODE)). Immediately prior to analysis, one volume of $H_2O$ was added to five volumes methanol-suspended sample, which was then passed through a 0.22 μm filter (Millipore Corporation, Bedford, Mass.). Sample (20 μl) was injected onto a Prodigy C-18 column (1×250 mm, 5 μm ODS, 100 A; Phenomenex, Rancho Palos Verdes, Calif.) at a flow rate of 50 μl/min. The separation was performed under isocratic conditions using 95% methanol in water as the mobile phase. In each analysis, the entirety of the HPLC column effluent was introduced onto a Quattro II triple quadrupole MS (Micromass, Inc.). Analyses were performed using electrospray ionization in negative-ion mode with multiple reaction monitoring (MRM) of parent and characteristic daughter ions specific for the isomers monitored. The transitions monitored were mass-to-charge ratio (m/z) 295 171 for 9-HODE; m/z 319 151 for 9-HETE; m/z 327 184 for 12-HETE-d8. $N_2$ was used as the curtain gas in the electrospray interface. The internal standard 12-HETE-d8 was used to calculate extraction efficiencies (which were >80% for all analyses). External calibration curves constructed with authentic standards were used to quantify 9-HETE and 9-HODE.

b) RP-HPLC Quantification of CE-H(P)ODEs

Sample (100 µl) reconstituted in methanol (without base hydrolysis) were injected onto a Beckman C-18 column (4.6×250 mm, 5 µm ODS; Beckman Instruments, Inc., Fullerton, Calif.). Lipids were separated using an isocratic solvent system comprised of 2-isopropanol/acetonitrile/water (44/54/2, v/v/v) at a flow rate of 1.5 ml/min. CE-H(P) ODEs were quantified as their stable hydroxide forms by UV detection at 234 nm using CE-9-HODE (Cayman Chemical Company, Ann Arbor, Mich.) for generation of an external calibration curve.

Results

Figure 4:
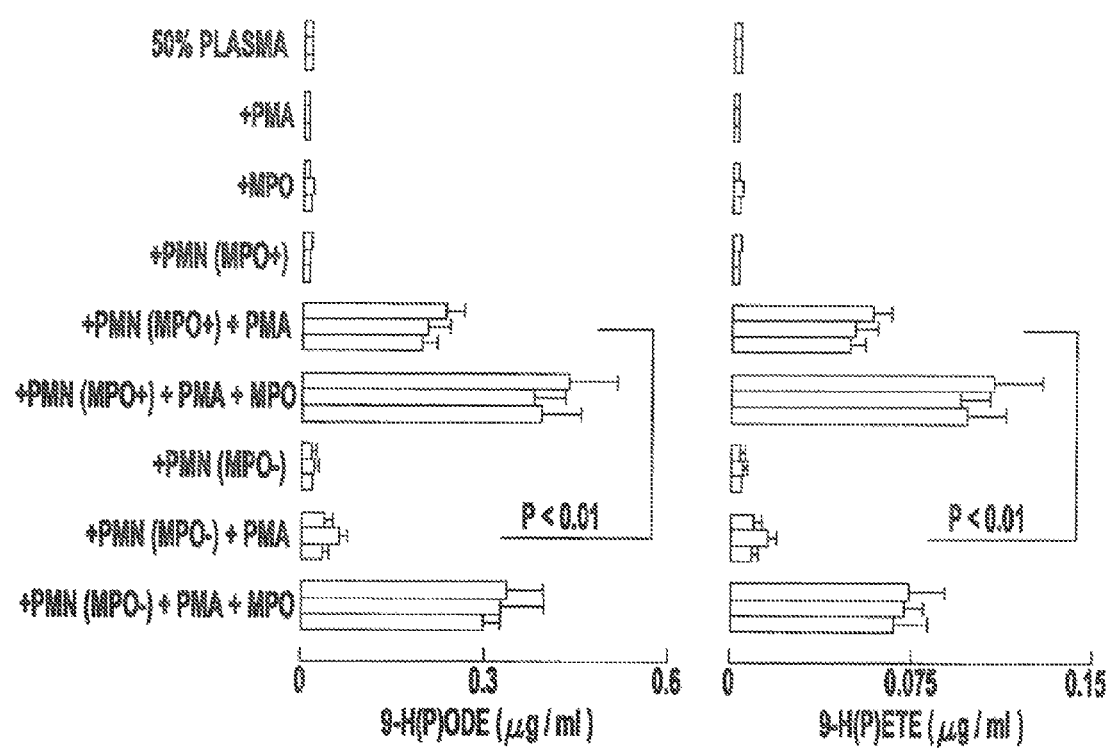
FIG. 4. Lipid Peroxidation in Plasma with Neutrophils from Healthy Subjects and MPO Deficient Subjects. Neutrophils ($1 \times 10^6$/ml) isolated from normal and MPO-deficient individuals were incubated at 37° C. in HBSS supplemented with DTPA (100 μM, pH 7.0) and fresh human plasma (50% v/v). Cells were activated by addition of phorbol myristate acetate (PMA, 200 nM) and incubated for 2 h (Complete System). The content of 9-H(P)ODE and 9-H(P)ETE formed within endogenous plasma lipids were then determined by LC/ESI/MS/MS. Where indicated, human MPO (30 nM) was added to reaction mixtures. Data represent the mean±SD of triplicate determinations. Each bar within a cluster for a given condition represents results obtained from independent experiments performed with neutrophil preparations from a distinct donor. PMN(MPO+), neutrophils isolated from normal subjects; PMN(MPO−), neutrophils isolated from MPO-deficient subjects.

Normal neutrophils generated significant levels of 9-H(P) ODE and 9-(H)PETE in plasma following cell activation by PMA (FIG. 4). In stark contrast, MPO-deficient neutrophils failed to generate significant levels of lipid peroxidation products following stimulation with PMA, despite their enhanced capacity to produce $O_2^{\cdot-}$. Addition of catalytic amounts of MPO restored the capacity of MPO-deficient neutrophils to initiate peroxidation of endogenous plasma lipids (FIG. 4).

Figure 5:
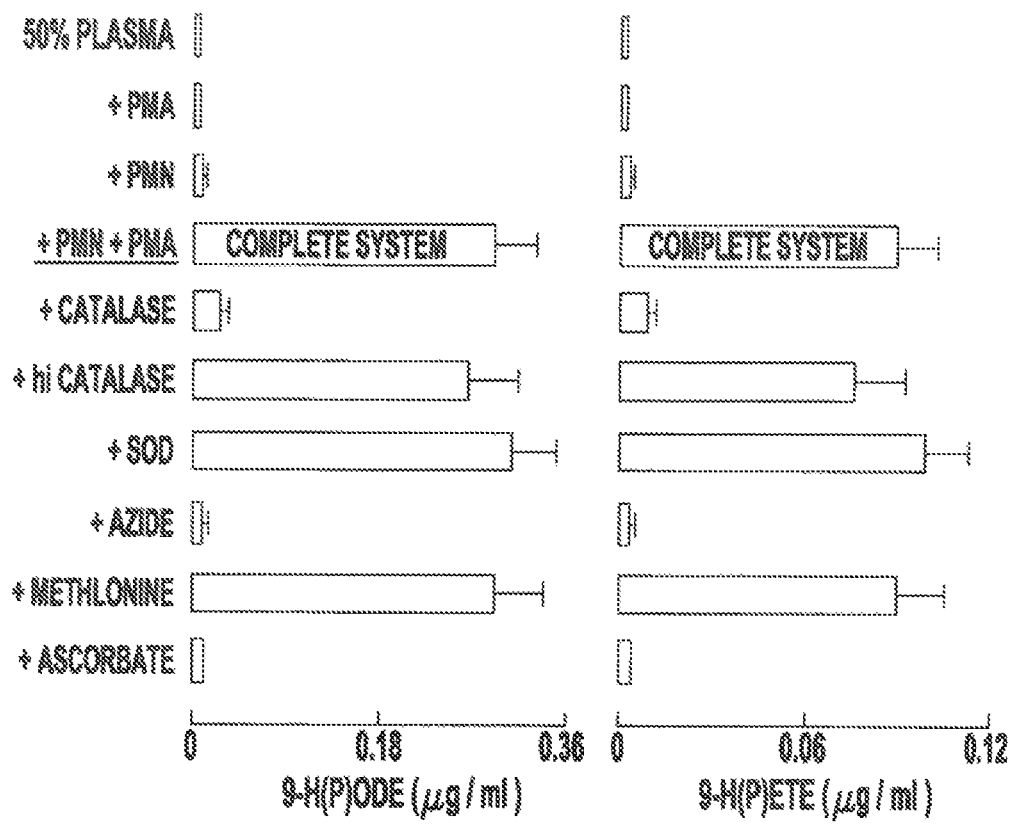
FIG. 5. Characterization of neutrophil-dependent initiation of lipid peroxidation of endogenous plasma lipids. Neutrophils ($1 \times 10^6$/ml) isolated from normal subjects (PMN) were incubated at 37° C. in HBSS supplemented with DTPA (100 μM, pH 7.0) and fresh human plasma (50% v/v). Cells were activated by addition of phorbol myristate acetate (PMA, 200 nM) and then incubated for 2 h (Complete System). The content of 9-H(P)ODE and 9-H(P)ETE formed within endogenous plasma lipids were then determined by LC/ESI/MS/MS. Additions or deletions to the Complete System were as indicated. The final concentrations of additions to the Complete System were 30 nM human MPO, 1 mM $NaN_3$, 300 nM catalase (Cat), 300 nM heat inactivated-catalase (hiCat), 100 μM methionine (Met), 100 μM ascorbate and 10 μg/ml superoxide dismutase (SOD). Data represent the mean±SD of three independent experiments.

Addition of catalase, but not heat inactivated catalase, to cell mixtures resulted in the near complete ablation of lipid peroxidation in plasma, strongly suggesting a critical role for $H_2O_2$ in the cell-dependent reaction (FIG. 5). Incubation of reaction mixtures with superoxide dismutase (SOD) failed to attenuate oxidation of plasma lipids (FIG. 5). In contrast, addition of heme poisons (e.g. azide, cyanide) and the water-soluble antioxidant ascorbate resulted in complete inhibition of neutrophil-depended peroxidation of plasma lipids. Finally, addition of HOCl scavengers such as dithiothreitol and the thioether methionine, failed to attenuate neutrophil-dependent peroxidation of endogenous plasma lipids, assessed by quantification of 9-H(P)ODE and 9-H(P)ETE (FIG. 5).

Figure 6:
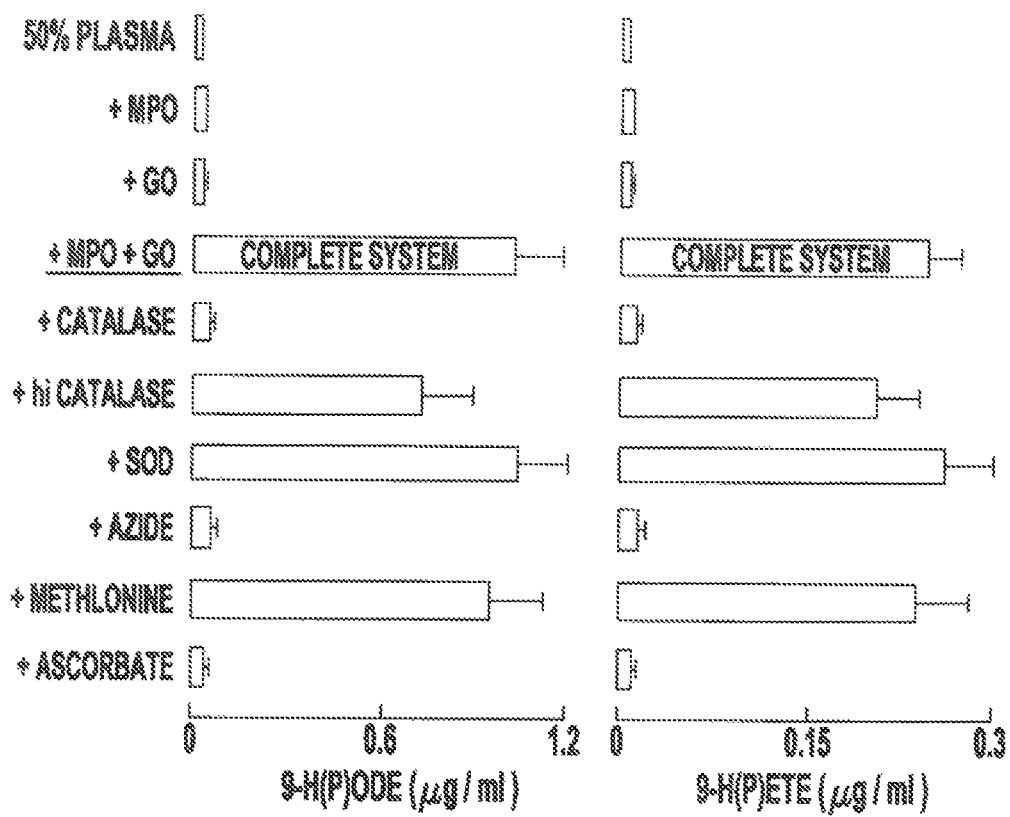
FIG. 6. Characterization of MPO-dependent initiation of lipid peroxidation of endogenous plasma lipids. Fresh human plasma (50%, v/v) was incubated with isolated human MPO (30 nM) at 37° C. in HBSS supplemented with DTPA (100 μM, pH 7.0) and a $H_2O_2$-generating system comprised of glucose/glucose oxidase (G/GO) for 12 h (Complete System). Under this condition, a continuous flux of $H_2O_2$ is formed at 10 μM/hr. The content of 9-H(P)ODE and 9-H(P)ETE formed within endogenous plasma lipids were then determined by LC/ESI/MS/MS. Additions or deletions to the Complete System were as indicated. The final concentrations of additions to the Complete System were 1 mM $NaN_3$, 300 nM catalase (Cat), 300 nM heat-inactivated catalase (hiCat), 200 nM SOD, 100 µM methionine (Met), and 100 µM ascorbate. Data represent the mean±SD of three independent experiments.

Results thus far presented strongly suggest that neutrophils employ the MPO-$H_2O_2$ system to generate reactive species distinct from chlorinating intermediates as the primary oxidants for initiation of lipid peroxidation in plasma. To confirm a physiological role for MPO, we next added purified human MPO and a $H_2O_2$-generating system (glucose/glucose oxidase, G/GO) to plasma and monitored formation of specific oxidation products by LC/ESI/MS/MS analysis. Formation of 9-H(P)ODE and 9-H(P)ETE occurred readily and had an absolute requirement for the presence of both MPO and the $H_2O_2$-generating system (FIG. 6). Lipid oxidation was again inhibited by catalase, azide or ascorbate, but was not affected by addition of SOD or methionine (FIG. 6). Collectively, these results strongly support a pivotal role for the MPO-$H_2O_2$ system of leukocytes as a primary mechanism for initiating lipid peroxidation in complex biological tissues and fluids such as plasma.

MPO Oxidation of LDL and the Presence of the Resultant Oxidation Products in Atherosclerotic Lesions General procedures. Human myeloperoxidase (donor: hydrogen peroxide, oxidoreductase, EC 1.11.1.7) and LDL were isolated and quantified as described (Podrez, E. A, et al., 1999, *J. Clin. Invest.* 103:1547). All buffers were treated with Chelex-100 resin (Bio-Rad, Hercules, Calif.) and supplemented with diethylenetriaminepentaacetic acid (DTPA) to remove trace levels of transition metal ions that might catalyze LDL oxidation during incubations. LDL was labeled with Na[$^{125}$I] to a specific activity between 100 and 250 dpm/ng protein, as described (Hoppe, G., et al., 1994, *J. Clin. Invest.* 94, 1506-12). Extraction of cellular lipids and thin-layer chromatography separation of radiolabeled cholesterol esters and free cholesterol were performed as described (Podrez, E. A, et al., 1999, *J. Clin. Invest.* 103: 1547). Incorporation of [$^{14}$C]oleate into cholesteryl esters by cells following incubation with the indicated lipoproteins (50 µg/ml), were determined as described (Podrez, E. A, et al., 1999, *J. Clin. Invest.* 103:1547). Rabbit thoracic aortae were isolated from WHHL Rabbits, rinsed in argon-sparged PBS supplemented with 100 µM butylated hydroxytoluene (BHT) and 100 µM DTPA, submerged in the same buffer, covered in argon and flash frozen in liquid nitrogen and then stored at −80° C. until analysis. Aortae relatively free of lipid lesions were obtained from WHHL rabbits age 10-12 weeks, while aortae full of lesions were recovered from WHHL rabbits greater than 6 months old.

Lipoprotein modification. LDL modified by MPO-generated nitrating intermediates ($NO_2$-LDL) was formed by incubating LDL (0.2 mg protein/ml) at 37° C. in 50 mM sodium phosphate, pH 7.0, 100 µM DTPA, 30 nM MPO, 100 µg/ml glucose, 20 ng/ml glucose oxidase and 0.5 mM $NaNO_2$ for 8 h unless otherwise specified. Under these conditions, a constant flux of $H_2O_2$ (10 µM/hr) is generated by the glucose/glucose oxidase system, as determined by the oxidation of Fe(II) and formation of Fe(III)-thiocyanate complex (van der Vliet, A., et al., 1997, *J. Biol. Chem.*, 272:7617). Oxidation reactions were terminated by addition of 40 µM BHT and 300 nM catalase to the reaction mixture. LDL acetylation was performed as described earlier (Podrez, E. A., et al., 1999, *J. Clin. Invest.* 103:1547).

Phospholipid separation and mass spectrometric analysis. Lipids were maintained under inert atmosphere (argon or nitrogen) at all times. Lipids from either oxidized PAPC or PLPC vesicles, or from $NO_2$-LDL, were extracted three times sequentially by the method of Bligh and Dyer [Bligh, 1959 #52] immediately after adding an equal volume of saturated NaCl solution (to enhance lipid extraction). The combined chloroform extracts were evaporated under nitrogen, and lipids were then resuspended in methanol (at approximately 200 g/0.1 mL), filtered through an Acrodisc CR PTFE filter and applied on a reverse-phase column (Luna C18, 250×10 mm, 5 µm, Phenomenex, Torrence, Calif., USA). Lipids were resolved at a flow rate of 3 mL/min using a ternary (acetonitrile/methanol/$H_2O$) gradient generated by a Waters 600 E Multisolvent delivery system HPLC (Waters, Milford, Mass., USA), and monitored using an evaporative light scattering detector (Sedex 55, Sedere, Alfortville, France).

Further fractionation and isolation of bioactive lipids was performed on combined lipid extracts from three separations that were dried under $N_2$, resuspended in chloroform (300 µl) supplemented with BHT and maintained under argon atmosphere. An aliquot of the fraction (⅔rds) was removed, evaporated under nitrogen and resuspended in HPLC buffer (methanol/water; 85/15; v/v) immediately prior to injection on reverse phase HPLC column.

Mass spectrometric analyses were performed on a Quatro II triple-quadrupole mass spectrometer (Micromass, Inc., Altrincham, U.K.) equipped with an electrospray ionization (ESI) probe and interfaced with an HP 1100 HPLC (Hewlett-Packard, Wilmington, Del.). Lipids (both free and following derivatization) were resolved on a Luna C18 250×4.6 mm, 5 μm column (Phenomenex, Torrance, Calif.) at a flow rate of 0.8 ml/min. A discontinuous gradient (Gradient II) was used by mixing solvent A (methanol (MeOH):$H_2O$, 85:15, v:v) with solvent B (MeOH), as follows: isocratic elution with solvent A from 0-7 min; increasing to 88% solvent B from 7-10 min; increasing to 91% solvent B from 10-34 min; and then increasing to 94% solvent B from 34-52 min). The column effluent was split such that 45 μl/min was introduced to the mass spectrometer and 755 l/min was collected and analyzed for biological activity. In some cases, biological activity was also determined using the same gradient following injection of authentic standards. Mass spectrometric analyses were performed on-line using electrospray ionization tandem mass spectrometry (ESI/MS/MS) in the positive ion mode with multiple reaction monitoring (MRM) mode (cone potential 60 eV/collision energy 20-25 eV). The MRM transitions used to detect the oxidized phosphopholipids present in each fraction were the mass to charge ratio (m/z) for the molecular cation $[MH]^+$ and the daughter ion m/z 184, the phosphocholine group (i.e. $[MH]^+ \rightarrow$ m/z 184). Oxime derivatives of phospholipids were monitored at m/z $[MH+29]^+ \rightarrow$ m/z 184.

Figure 3:
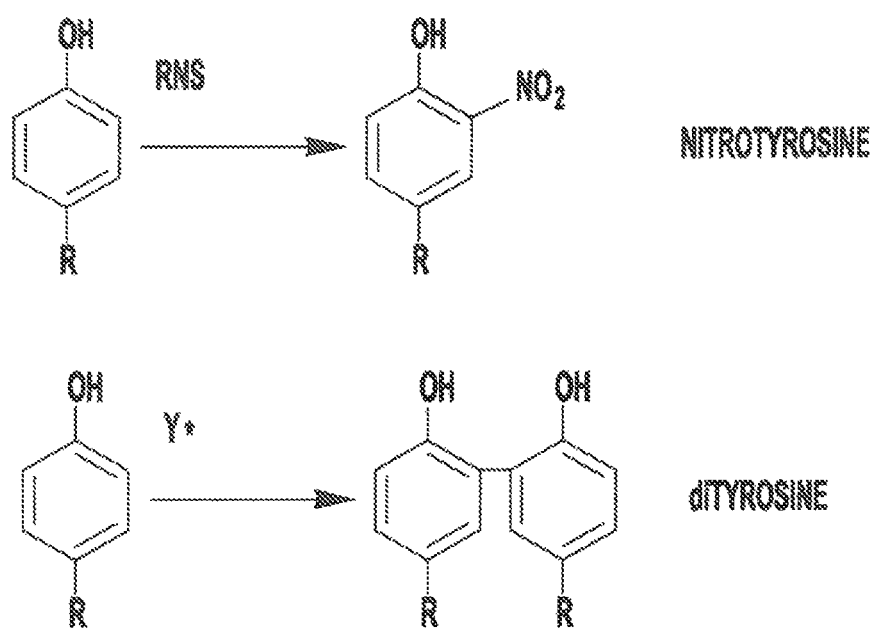
FIG. 3. The chemical structure of dityrosine and nitrotyrosine.

Quantification of the various oxidized PC species was performed using LC/ESI/MS/MS in positive ion mode using MRM. Formic acid (0.1%) was included in the mobile phases. Distinct oxidized phospholipid species were identified by using m/z for protonated parent→daughter transitions specific for each individual phospholipid and their retention times, as illustrated in FIGS. 2 and 3. OV-PC and ND-PC were quantified similarly but by also monitoring at the m/z for the transition between the hemiacetal formed with methanol for each analyte and the loss of polar head group (m/z 184).

Lipids were initially extracted three times by the method of Bligh and Dyer (Bligh, E. G., et al., 1959, *Canadian Journal of Biochemical Physiology*, 37, 911-917) from lipoproteins or tissues in the presence of BHT. The combined extracts were rapidly dried under nitrogen, resuspended in methanol:$H_2O$ (98:2, v:v), and then neutral lipids in the lipid extracts were removed by passage through a 18 C minicolumn (Supelclean LC-18 SPE tubes, 3 ml; Supelco Inc., Bellefonte, Pa.). A known amount of dimyristyl phosphatidyl choline (DMPC) was added to the polar lipid fraction as an internal standard, and the lipids were dried under nitrogen and stored under an argon atmosphere at −80° C. until analysis within 24 h. Calibration curves were constructed with a fixed amount of DMPC and varying mol % of each synthetic oxidized PC species and used to correct for the differences in ionization response factors observed amongst the different lipids. In additional preliminary studies the quantification methods employed were independently validated for each analyte by demonstrating identical results to those obtained by the method of standard additions

Results

Figure 7:
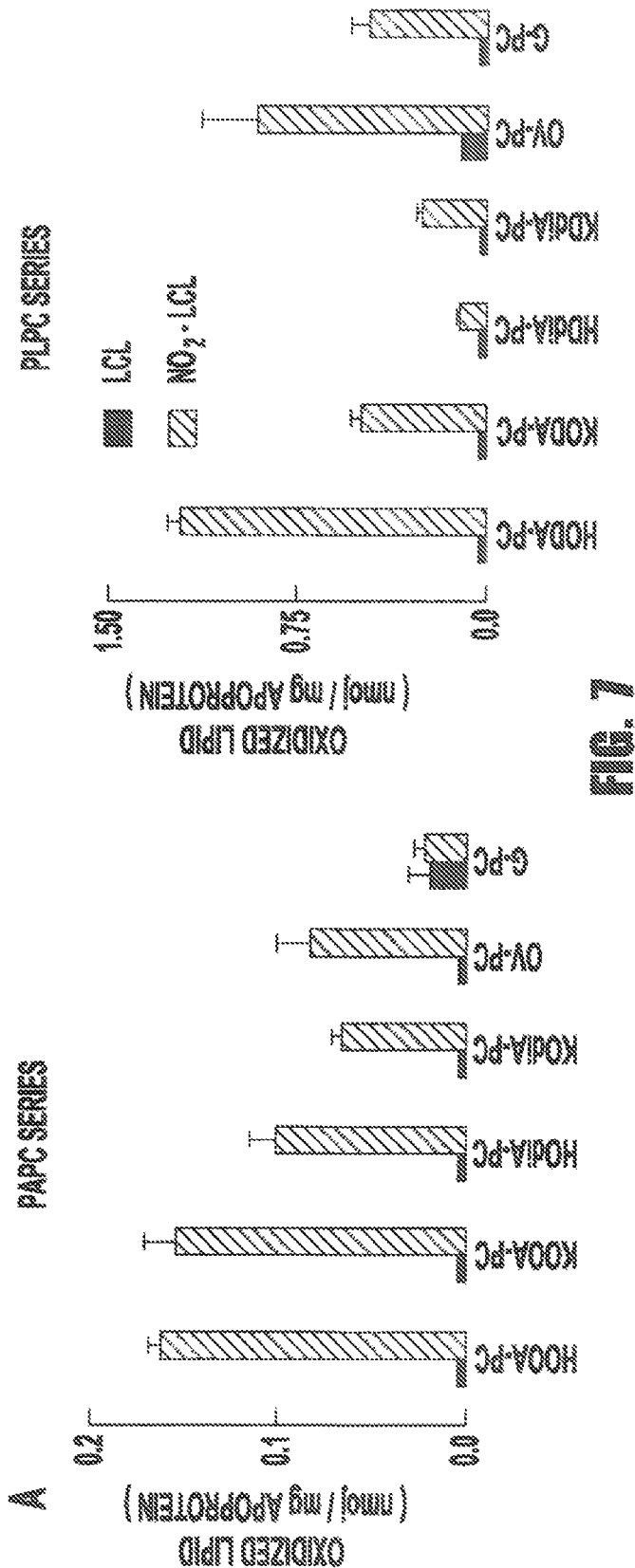
FIG. 7. Oxidized phosphatidyl choline species generated by MPO oxidation of LDL are enriched in atherosclerotic lesions. The contents of the indicated oxidized PC species were determined in native LDL and LDL oxidized by the $MPO-H_2O_2-NO_2$ system ($NO_2$-LDL) using LC/ESI/MS/MS. Data represent the mean±S.D. of triplicate determinations of a representative experiment performed two times. The content of PAPC in LDL and $NO_2$-LDL preparations were 0.122±0.07 and 0.008±0.001 µmol/mg apoprotein, respectively. The content of PLPC in LDL and $NO_2$-LDL preparations were 0.88±0.05 and 0.35±0.05 µmol/mg apoprotein, respectively. The thoracic aorta from Watanabe Heritable Hyperlipidemic Rabbits was isolated, rinsed in Argon sparged PBS supplemented with 100 µM BHT and 100 µM DTPA, submerged in the same buffer, covered in argon, flash-frozen in liquid nitrogen and then stored at –80° C. until analysis. Aortae relatively free of lipid lesions were obtained from WHHL rabbits age 10-12 weeks, while aortae with confluent lesions were recovered from WHHL rabbits>6 months old. Individual frozen aortae were pulverized with stainless steel mortar and pestle under liquid nitrogen, the powder transferred to glass screw capped test tubes equipped with PTFE-lined caps, and then lipids were extracted by the method of Bligh and Dyer under Argon in the presence of BHT. Three aortae were analyzed in each group. Quantification of lipids was then performed by LC/ESI/MS/MS. Data are expressed as mean±S.D.

Quantification of various specific oxidated PC species by LC/ESI/MS/MS analysis in native and oxidized forms of LDL revealed substantial increases in the content of oxidated phosphatidyl choline species (FIG. 7a, data for native LDL, $NO_2$-LDL shown). Regardless of what time point of oxidation was examined, HODA-PC and HOOA-PC were major products of LDL oxidation by MPO. The combined mol % (relative to remaining unoxidized phospholipids) and ND-PC) detected in $NO_2$-LDL (FIG. 7a) correspond to ~1.2 mol %. Of these, the combined content of the 8 oxidized PC species quantified in $NO_2$LDL preparation (FIG. 7a) correspond to 0.73 mol %.

To determine if oxidized PC species are formed in vivo, thoracic aortae with and without extensive atherosclerotic lesions were isolated from Watanabe heritable hyperlipidemic (WHHL) rabbits and the levels of multiple distinct specific oxidized phospholipids were determined using LC/ESI/MS/MS analyses. Significant increases in the content of each of the oxidized PCs derived from oxPAPC (HOOA-PC, KOOA-PC, HOdiA-PC, KOdiA-PC) and oxPLPC (HODA-PC, KODA-PC, HDdiA-PC and KDdiA-PC) were noted in the diseased vessels (FIG. 7b). Interestingly, while the levels of oxidized PC species derived from PLPC were lower than that observed for the more highly oxidized ON-PC and ND-PC, levels of oxidized PC species derived from PAPC were comparable to that observed for OV-PC and G-PC (FIG. 7a).

Figure 8:
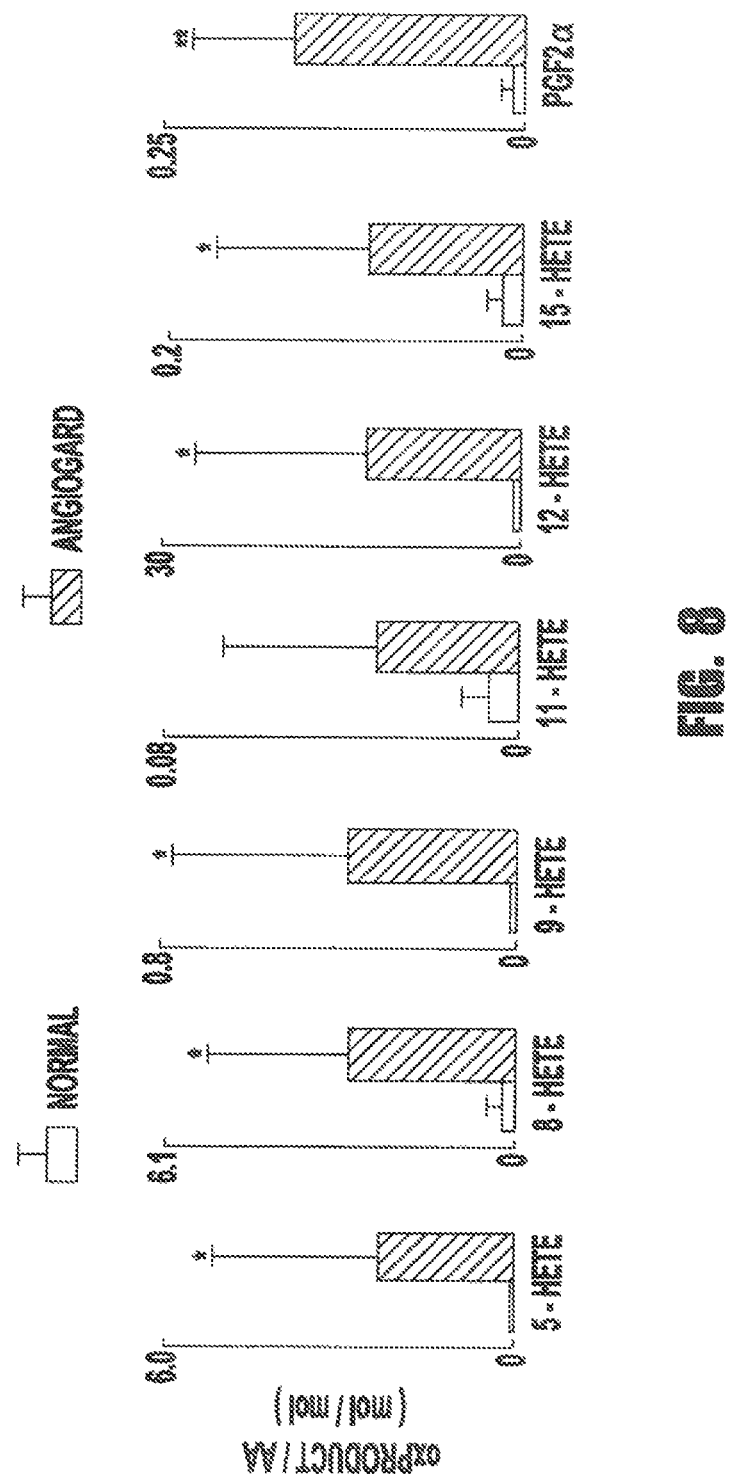
FIG. 8. Content of select MPO-gGenerated oxidized lipids in atherosclerotic plague material of human patients and normal aortic intima of heart transplant donors.

Presence of HETEs, HODEs, F2 Isoprostanes and Oxidized PC Species in Atherscloerotic Lesions of Human Subjects The Angiogard is an emboli-protection device recently invented for use during percutaneous vascular interventions. It is deployed distal to the target lesion prior to balloon inflation for angioplasty. It serves as a temporary umbrella, catching extruded lipid-rich plaque material through an inert sieve-like mesh. The pores of the mesh are large and microscopy confirms that they do not obstruct flow of blood cells or platelets, but rather capture large lipid globules. The material captured in the Angiogard at the time of intervention was analyzed to determine the lipid species in the plaque material. FIG. 8 shows the levels of multiple distinct lipid oxidation products quantified by LC/ESI/MS/MS methods in plaque material recovered from the Angiogard. For comparison, we also assessed the levels of the same oxidized lipids in normal aortic intima recovered at the time of organ harvest from heart transplant donors. Dramatic increases in $F_2$-Isoprostanes and each of the HETEs monitored were observed. Analysis of plaque material captured in the Angiogard also confirmed detection of multiple distinct oxPC species (data not shown).

Methods of Determining Levels of Select Myeloperoxidase-Generated Oxidation Products A. Dityrosine and Nitrotyrosine Dityrosine and nitrotyrosine levels in the bodily sample can be determined using monoclonal antibodies that are reactive with such tyrosine species. For example, anti-nitrotyrosine antibodies may be made and labeled using standard procedures and then employed in immunoassays to detect the presence of free or peptide-bound nitrotyrosine in the sample. Suitable immunoassays include, by way of example, radioimmunoassays, both solid and liquid phase, fluorescence-linked assays or enzyme-linked immunosorbent assays. Preferably, the immunoassays are also used to quantify the amount of the tyrosine species that is present in the sample.

Monoclonal antibodies raised against the dityrosine and nitrotyrosine species are produced according to established procedures. Generally, the dityrosine or nitrotyrosine residue, which is known as a hapten, is first conjugated to a carrier protein and used to immunize a host animal. Preferably, the dityrosine and nitrotyrosine residue is inserted into synthetic peptides with different surrounding sequence and then coupled to carrier proteins. By rotating the sequence surrounding the dityrosine and nitrotyrosine species within the peptide coupled to the carrier, antibodies to only the dityrosine and nitrotyrosine species, regardless of the surrounding sequence context, are generated. Similar strategies have been successfully employed with a variety of other low molecular weight amino acid analogues.

Suitable host animals, include, but are not limited to, rabbits, mice, rats, goats, and guinea pigs. Various adjuvants may be used to increase the immunological response in the host animal. The adjuvant used depends, at least in part, on the host species. To increase the likelihood that monoclonal antibodies specific to the dityrosine and nitrotyrosine are produced, the peptide containing the respective dityrosine and nitrotyrosine species may be conjugated to a carrier protein which is present in the animal immunized. For example, guinea pig albumin is commonly used as a carrier for immunizations in guinea pigs. Such animals produce heterogenous populations of antibody molecules, which are referred to as polyclonal antibodies and which may be derived from the sera of the immunized animals.

Monoclonal antibodies, which are homogenous populations of an antibody that binds to a particular antigen, are obtained from continuous cells lines. Conventional techniques for producing monoclonal antibodies are the hybridoma technique of Kohler and Millstein (Nature 356: 495-497 (1975)) and the human B-cell hybridoma technique of Kosbor et al (Immunology Today 4:72 (1983)). Such antibodies may be of any immunoglobulin class including IgG, IgM, IgE, Iga, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. *Methods Enzymol.* 269:201-209.

In general, techniques for direct measurement of protein bound dityrosine and nitrotyrosine species from bodily fluids involves removal of protein and lipids to provide a fluid extract containing free amino acid residues. The tissues and bodily fluids are stored, preferably in buffered, chelated and antioxidant-protected solutions, preferably at −80° C. as described above. The frozen tissue, and bodily fluids are then thawed, homogenized and extracted, preferably with a single phase mixture of methanol:diethylether:water as described above to remove lipids and salts. Heavy isotope labeled internal standards are added to the pellet, which, preferably, is dried under vacuum, hydrolyzed, and then the amino acid hydrolysate resuspended, preferably in a water:methanol mixture, passed over a mini solid-phase C18 extraction column, derivatized and analyzed by stable isotope dilution gas chromatography-mass spectrometry as above. Values of free dityrosine and nitrotyrosine species in the bodily sample can be normalized to protein content, or an amino acid such as tyrosine as described above.

In a highly preferred procedure, protein is delipidated and desalted using two sequential extractions with a single phase mixture of $H_2O$/methanol/$H_2O$-saturated diethyl ether (1:3:8 v/v/v). Oxidized tyrosine standards (2 pmol each) and universal labeled tyrosine (2 nmol) are added to protein pellets. Proteins are hydrolyzed by incubating the desalted protein pellet with degassed 6N HCl supplemented with 1% phenol for 24 h under argon atmosphere. Amino acid hydrolysates are resuspended in chelex treated water and applied to mini solid-phase C18 extraction columns (Supelclean LC-C18SPE minicolumn; 3 ml; Supelco, Inc., Bellefonte, Pa.) pre-equilibrated with 0.1% trifluoroacetic acid. Following sequential washes with 2 ml of 0.1% trifluoroacetic acid, oxidized tyrosines and tyrosine are eluted with 2 ml 30% methanol in 0.1% trifluoroacetic acid, dried under vacuum and then analyzed by mass spectrometry.

Tandem mass spectrometry is performed using electrospray ionization and detection with an ion trap mass spectrometer (LCQ Deca, ThermoFinigann, San Jose, Calif.) interfaced with a Thermo SP4000 high performance liquid chromatograph (HPLC). Samples are suspended in equilibration solvent ($H_2O$ with 0.1% formic acid) and injected onto a Ultrasphere C18 column (Phenominex, 5 µm, 2.0 mm×150 mm). L-Tyrosine and its oxidation products are eluted at a flow rate of 200 µl/min using a linear gradient generated against 0.1% formic acid in methanol, pH 2.5 as the second mobile phase. Analytes are monitored in positive ion mode with full scan product ion MS/MS at unit resolution. Response is optimized with a spray voltage setting of 5 KV and a spray current of 80 pA. The heated capillary voltage is set at 10 V and the temperature to 350° C. Nitrogen is used both as sheath and auxiliary gas, at a flow rate of 70 and 30 arbitrary units, respectively. The analyte abundance is evaluated by measuring the chromatographic peak areas of selected product ions extracted from the full scan total ion chromatograms, according to the corresponding ion trap product ion spectra. The ions monitored for each analyte are: 3-nitro[$^{12}C_6$]tyrosine (mass-to-charge-ratio (m/z) 227, 181 and 210), 3-nitro[$^{13}C_6$]tyrosine (m/z 233, 187 and 216), 3-nitro[$^{13}C_9^{15}N_1$]tyrosine (m/z 237, 190 and 219), [$^{12}C_6$]tyrosine (m/z 182, 136 and 165), [$^{13}C_9^{15}N_1$]tyrosine (m/z 192, 145 and 174). Tyrosine and nitrotyrosine are base-line resolved under the HPLC conditions employed, permitting programming of the LCQ Deca for analysis over 0-7 min for detection of tyrosine isotopomers, and from 7 min on for detection of 3-nitrotyrosine isotopomers.

Free nitrotyrosine and dityrosine are similarly measured in samples, but tissue or bodily fluid is first passed through a low molecular weight cut off filter and the low molecular weight components analyzed by LC/ECS/MS/MS. Values of free and protein-bound dityrosine and nitrotyrosine species in the bodily sample can be normalized to protein content, or an amicon acid such as the precursor tyrosine, as described below.

B. Lipid Oxidation Products

Lipid oxidation products can be measured by HPLC with UV detection or HPLC with on line mass spectrometry. Other analytical methods including GC/MS and immunocytochemical methods may also be used. F2Isoprostanes are measurable by various mass spectrometry techniques as known in the art.

Methods of extracting and quantifying the MPO-generated lipid oxidation products hydroxy-eicosatetraenoic acids (HETEs), hydroxy-octadecadienoic acids (HODEs), F2Isoprostanes; the 5-oxovaleric acid esters of 2-lysoPC (OV-PC); 5-cholesten-5α,6α-epoxy-3β-ol (cholesterol α-epoxide); 5-cholesten-5β,6β-epoxy-3β-ol (cholesterol β-epoxide); 5-cholesten-3β,7β-diol (7-OH-cholesterol); 5-cholesten-3β,25-diol (25-OH cholesterol 5-cholesten-3β-ol-7β-hydroperoxide (7-OOH cholesterol); and cholestan-3β,5α,6β-triol (triol). are described in Schmitt, et al. (1999) *Biochemistry*, Vol. 38, 16904-16915, which is specifically incorporated herein by reference. For determination of 9-H(P)ODE, 9-H(P)ETE and $F_2$-isoprostanes, hydroperoxides in reaction mixtures are reduced to their corresponding hydroxides during extraction utilizing a modified Dole procedure in which the reducing agent, triphenylphosphine, is present (Savenkova, M. L., et al. (1994) *J. Biol. Chem.* 269, 20394-20400). These conditions also inhibit artifactual formation of isoprostanes and oxidized lipids. Lipids are dried under $N_2$, resuspended in isopropanol (2 ml) and then fatty acids released by base hydrolysis with 1 N sodium hydroxide (2 ml) at room temperature under $N_2$ for 90 min. The samples are acidified (pH 3.0) with 2N HCl, known amounts of internal standards are added and free fatty acids are extracted twice with hexane (5 ml). The content of 9-H(P) ODEs, 9-H(P)ETEs and $F_2$-isoprostanes are then determined by LC/MS/MS analysis as outlined below.

1-palmitoyl-2 oxovaleryl-sn-glycero-3-phosphatidyl choline (PoxvPC) is extracted by the same modified Dole procedure used for 9-H(P)ODE, 9-H(P)ETE and $F_2$ isoprostane analyses as above, but omitting addition of the reductant, triphenylphosphine. Lipids are dried under $N_2$, resuspended in methanol and stored under argon at $-70°$ C. until subsequent LC/MS analysis as outline below. Sterol oxidation products are extracted by adding 4 M NaCl (150 μl) and acetonitrile (500 μl). Samples are vortexed, centrifuged, and the upper organic phase removed. Extracts are dried under $N_2$, resuspended in methanol, and stored under argon at $-70°$ C. until analysis by HPLC with on-line mass spectrometric analysis.

Mass spectrometric analyses are performed on a Quatro II triple quadruple mass spectrometer interfaced with an HP 1100 HPLC. $F_2$-isoprostanes are quantified by stable isotope dilution mass spectrometry using on-line reverse phase HPLC tandem mass spectrometry (LC/MS/MS) with 8-epi-[$^2H_4$]PGF$_{2\alpha}$ as standard as described by Mallat (Mallat, Z., et al. (1999) *J. Clin. Invest.* 103, 421-427). For 9-HODE and 9-HETE analyses, lipid extracts generated following base hydrolysis of reduced lipids (above) are dried under $N_2$ and reconstituted in methanol. An aliquot of the mixture is then injected on an Ultrasphere ODS C18 column equilibrated and run under isocratic conditions employing methanol: $H_2O$, (85:15, v/v) as solvent. Column eluent is split (930 μl/min to UV detector and 70 μl/min to mass detector) and analyzed by the mass spectrometer. LC/MS/MS analysis of 9-HODE, 9-HETE and $F_2$-isoprostanes in column effluents is performed using electrospray ionization mass spectrometry (ESI-MS) in the negative-ion mode with multiple reaction monitoring (MRM) and monitoring the transitions m/z 295→171 for 9-HODE; m/z 319→151 for 9-HETE; m/z 353→309 for $F_2$-isoprostanes; and m/z 357→313 for [$^2H_4$]PGF$_{2\alpha}$.

Quantification of POxvPC is performed on lipid extracts utilizing HPLC with on-line ESI-MS analysis in the positive ion mode and selected ion monitoring at m/z 782 and m/z 594, respectively. An aliquot of lipid extract reconstituted in methanol (above) is mixed 0.1% formic acid in methanol (mobile phase B) and loaded onto a Columbus C18 column (1×250 mm, 5 μm, P. J. Cobert, St. Louis, Mo.) pre-equilibrated in 70% mobile phase B, 30% mobile phase A (0.1% formic acid in water) at a flow rate of 30 μl/min. Following a 3 min wash period at 70% mobile phase B, the column is developed with a linear gradient to 100% mobile phase B, followed by isocratic elution with 100% mobile phase B. External calibration curves constructed with authentic POxvPC are used for quantification. 7-OH cholesterol, 7-keto cholesterol, and 7-OOH cholesterol are resolved on an Ultrasphere ODS C18 column. The elution gradient consisted of 91:9, acetonitrile:water+0.1% formate (v:v), and the column washed between runs with acetonitrile+0.1% formate. Column effluent is split (900 μl/min to UV detector and 100 μl/min to mass detector) and ionized by atmospheric pressure chemical ionization (APCI) in the positive-ion mode with selected ion monitoring. Identification of 7-OH cholesterol is performed by demonstrating co-migration of ions with m/z 385.3 $(M-H_2O)^+$ and m/z 367.3 $(M-2H_2O)^+$ with the same retention time as authentic standard. The integrated area of the ion current for the peak monitored at m/z 367.3 is used for quantification. Identification of 7-OOH cholesterol is performed by demonstrating co-migration of ions with m/z 401.3 $(M-H_2O)^+$, m/z 383.3 $(M-2H_2O)^+$ and m/z 367.3 $(M-H_2O_2)^+$ with the same retention time as authentic standard. The integrated area of the ion current for the peak monitored at m/z 401.3 is used for quantification. Identification of 7-keto cholesterol is performed by demonstrating co-migration of ions with m/z 401.3 $(M+H)^+$ and m/z 383.3 $(M-H_2O)^+$ with the same retention time as authentic standard. The integrated area of the ion current for the peak monitored at m/z 401.3 is used for quantification. External calibration curves constructed with authentic 7-OH cholesterol, 7-OOH cholesterol and 7-keto cholesterol are used for quantification following preliminary APCI LC/MS experiments demonstrating identical results to those obtained by the method of standard additions. The retention times for 25-OH cholesterol, 5,6α- and β-epoxides, and triol are determined by LC/MS analysis of authentic standards.

Predetermined Value

The level of MPO mass, MPO activity, or select MPO-generated oxidation product in the bodily sample obtained from the test subject is compared to a predetermined value. The predetermined value is based upon the levels of MPO activity, MPO mass, or select MPO-generated oxidation product in comparable samples obtained from the general population or from a select population of human subjects. For example, the select population may be comprised of apparently healthy subjects. "Apparently healthy", as used herein, means individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. Apparently healthy individuals also do not otherwise exhibit symptoms of disease. In other words, such individuals, if examined by a medical professional, would be characterized as healthy and free of symptoms of disease.

The predetermined value is related to the value used to characterize the level of MPO activity or MPO mass in the bodily sample obtained from the test subject. Thus, if the level of MPO activity is an absolute value such as the units of MPO activity per leukocyte or per ml of blood, the predetermined value is also based upon the units of MPO activity per leukocyte or per ml of blood in individuals in the general population or a select population of human subjects. Similarly, if the level of MPO activity or MPO mass is a representative value such as an arbitrary unit obtained from a cytogram, the predetermined value is also based on the representative value.

The predetermined value can take a variety of forms. The predetermined value can be a single cut-off value, such as a median or mean. The predetermined value can be established based upon comparative groups such as where the risk in one defined group is double the risk in another defined group. The predetermined can be a range, for example, where the general population is divided equally (or unequally) into groups, such as a low risk group, a medium risk group and a high-risk group, or into quadrants, the lowest quadrant being individuals with the lowest risk the highest quadrant being individuals with the highest risk.

The predetermined value can be derived by determining the level of MPO activity or mass in the general population. Alternatively, the predetermined value can be derived by determining the level of MPO activity or mass in a select population, such as an apparently healthy nonsmoker population. For example, an apparently healthy, nonsmoker population may have a different normal range of MPO activity or MPO mass than will a smoking population or a population whose member have had a prior cardiovascular disorder. Accordingly, the predetermined values selected may take into account the category in which an individual falls. Appropriate ranges and categories can be selected with no more than routine experimentation by those of ordinary skill in the art.

Predetermined values of MPO activity or MPO mass, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed. The standardized method that was used in Example 1 below employs the guaiacol oxidation assay as described in Klebanoff, S. J., Waltersdorph, A. N. and Rosen, H. 1984. "Antimicrobial activity of myeloperoxidase". Methods in Enzymology. 105: 399-403).

Comparison of MPO Activity and Mass Levels and Levels of Select MPO-Generated Oxidation Products in the Bodily Sample from the Test Subject to the Predetermined Value.

The levels of each risk predictor, i.e., MPO activity, MPO mass and select MPO-generated oxidation product, in the individual's bodily sample may be compared to a single predetermined value or to a range of predetermined values. If the level of the present risk predictor in the test subject's bodily sample is greater than the predetermined value or range of predetermined values, the test subject is at greater risk of developing or having CVD than individuals with levels comparable to or below the predetermined value or predetermined range of values. In contrast, if the level of the present risk predictor in the test subject's bodily sample is below the predetermined value or range of predetermined range, the test subject is at a lower risk of developing or having CVD individuals with levels comparable to or above the predetermined value or range of predetermined values. For example, a test subject who has a higher number of neutrophils or monocytes or both with elevated levels of MPO activity or MPO mass as compared to the predetermined value is at high risk of developing cardiovascular disease, and a test subject who has a lower number of neutrophils or monocytes or both with decreased or lower levels of MPO activity or MPO mass as compared to the predetermined value is at low risk of developing cardiovascular disease. The extent of the difference between the test subject's risk predictor levels and predetermined value is also useful for characterizing the extent of the risk and thereby, determining which individuals would most greatly benefit from certain aggressive therapies. In those cases, wherein the predetermined value ranges are divided into a plurality of groups, such as the predetermined value ranges for individuals at high risk, average risk, and low risk, the comparison involves determining into which group the test subject's level of the relevant risk predictor falls.

The present diagnostic tests are useful for determining if and when therapeutic agents which are targeted at preventing CVD should and should not be prescribed for a patient. For example, individuals with values of MPO activity (U/mg PMN protein; or U/ml blood) above a certain cutoff value, or that are in the higher tertile or quartile of a "normal range," could be identified as those in need of more aggressive intervention with lipid lowering agents, life style changes, etc.

One of the most attractive findings of increased MPO as a predictor of risk for CVD is that it represents an independent marker to identify individuals with increased risk for cardiovascular disease. That is, in multivariate analyses vs. other known risk factors for CVD (e.g. lipid levels such as LDL, HDL, total cholesterol, triglycerides, as well as family history, tobacco use, hypertension, diabetes), elevated levels of MPO activity and mass independently predicted association with CVD. Thus, the present diagnostic tests are especially useful to identify individuals at increased risk who might otherwise not have been identified by existing screening protocols/methods. Moreover, the present risk predictors can be used in combination with currently used risk predictors, such as blood LDL levels, blood triglyceride levels and blood C-reactive protein levels, and algorithms based thereon to more accurately characterize an individual's risk of developing or having CVD.

Evaluation of CVD Therapeutic Agents

The present diagnostic tests are also useful for evaluating the effect of CVD therapeutic agents on patients who have been diagnosed as having or as being at risk of developing CVD. Such therapeutic agents include, but are not limited to, anti-inflammatory agents, insulin sensitizing agents, antihypertensive agents, anti-thrombotic agents, anti-platelet agents, fibrinolytic agents, lipid reducing agents, direct thrombin inhibitors, ACAT inhibitor, CDTP inhibitor thioglytizone, and glycoprotein II b/IIIa receptor inhibitors. Such evaluation comprises determining the levels of one or more of the present risk predictors including MPO activity, MPO mass, select MPO-generated oxidation products, and combinations thereof, in a bodily sample taken from the subject prior to administration of the therapeutic agent and a corresponding bodily fluid taken from the subject following administration of the therapeutic agent. A decrease in the level of the selected risk factor in the sample taken after administration of the therapeutic as compared to the level of the selected risk factor in the sample taken before administration of the therapeutic agent is indicative of a positive effect of the therapeutic agent on cardiovascular disease in the treated subject.

EXAMPLES

The following examples are for purposes of illustration only and are not intended to limit the scope of the claims which are appended hereto.

Example 1

Levels of MPO Activity and MPO Mass in Blood Samples of Patients with and without Coronary Artery Disease Methods Study Population: Based on logistic regression power calculations (assuming equal size groups), 326 patients were needed to provide 80% power ($\alpha=0.05$) to detect a statistically significant odds ratio of at least 2.0 for high MPO (upper quartile). Subjects (n=333) were identified from two practices within the Cardiology Department of the Cleveland Clinic Foundation. First, a series of 85 consecutive patients were enrolled from the Preventive Cardiology Clinic. Simultaneously, 125 consecutive patients were enrolled from the catheterization laboratory. Based upon CAD prevalence in this series, a need for 116 additional control subjects was determined. All patients who did not have significant CAD upon catheterization over the preceding 6 months were identified from the catheterization database, and then 140 were randomly selected (based upon area code/telephone number) and invited to participate for MPO measurement. CAD was defined by a history of documented myocardial infarction, prior coronary revascularization intervention (CABG or percutaneous coronary intervention), or as the presence of ≥50% stenosis in one or more coronary arteries identified during cardiac catheterization. Exclusion criteria for the CAD group were an acute coronary event within 3 months preceding enrolment, end stage renal disease and bone marrow transplantation. The control group consisted of subjects who had undergone diagnostic coronary angiography that revealed no evidence of significant CAD. Exclusion criteria for control subjects were one or more coronary vessels with stenosis≥50%, valvular heart disease, left ventricle dysfunction, end-stage renal disease, bone marrow transplantation, or evidence of infection or active inflammatory diseases as revealed by history and exam. All patients were older than 45 years of age and afebrile. Clinical history was assessed for diabetes mellitus, smoking history past and present, hypertension and whether any first-degree relatives had CAD (men by the age of 50 years and females by the age of 60). Study protocol and consent forms were approved by the Cleveland Clinic Foundation Institutional Review Board and informed, written consent was obtained from all subjects. Samples were coded to ensure anonymity and all analyses were performed in a blinded fashion.

Measurements: Blood was drawn following an overnight fast into EDTA-containing tubes and used to quantify WBC, low density lipoprotein cholesterol (LDLc), high density lipoprotein cholesterol (HDLc), total cholesterol (TC) and fasting triglycerides (TG). Neutrophils were isolated by buoyant density centrifugation (Hazen, S. L., et al., *J. Biol. Chem.* 271:1861-1867). Cell preparations were at least 98% homogeneous by visual inspection. Leukocyte preparations were supplemented to 0.2% cetyltrimethylammonium bromide for cellular lysis, incubated at room temperature for 10 min, snap frozen in liquid nitrogen and stored at −80° C. until analysis.

Functional MPO was quantified by peroxidase activity assay of neutrophil lysates. Briefly, detergent-lysed cells ($10^4$/ml; triplicate samples) were added to 20 mM phosphate buffer (pH 7.0) containing 14.4 mM guaiacol, 0.34 mM $H_2O_2$, and 200 μM DTPA and the formation of guaiacol oxidation product monitored at $A_{470}$ at 25° C. (Klebanoff, S. J., et al., *Methods Enzymol.* 105:399-403, Capeillere-Blandin, C., *Biochem. J.* 36(Pt2):395-404). A millimolar absorbance coefficient of 26.6 $mM^{-1}cm^{-1}$ for the diguaiacol oxidation product was used to calculate peroxidase activity where one unit of MPO activity is defined as the amount that consumes 1 μmol of $H_2O_2$ per minute at 25° C. MPO activity reported is normalized either per mg of neutrophil protein (Leukocyte-MPO) or per ml of blood (Blood-MPO). Blood-MPO (Units MPO per ml of blood) was estimated by multiplying the units of MPO activity per neutrophil times the absolute neutrophil count (per microliter blood) times 1000. Protein concentration was determined as described (Markwell, M. A., et al., *Anal. Biochem.* 87:206-210).

Levels of Leukocyte-MPO in an individual were found to be extremely reproducible, demonstrating less than ±7% variations in subjects over time (n=6 males evaluated once per 1-3 months for >2 year period). The coefficient of variance for determination of Leukocyte-MPO, as determined by analysis of samples multiple times consecutively, was 4.2%. Leukocyte-MPO determination for 10 samples run on 3 separate days yielded a coefficient of variance of 4.6%. The coefficient of variance for determination of Blood-MPO as determined by analysis of samples multiple times consecutively, was 4.2%. Blood-MPO determination for 10 samples run on 3 separate days yielded a coefficient of variance of 4.8%. MPO mass per neutrophil was determined using an enzyme linked immunosorbent assay (ELISA). Capture plates were made by incubating 96-well plates overnight with polyclonal antibody (Dako, Glostrup, Denmark.) raised against the heavy chain of human MPO (10 μg/ml in 10 mM PBS, pH 7.2). Plates were washed and sandwich ELISA performed on leukocyte lysates using alkaline phosphatase-labeled antibody to human MPO. MPO mass was calculated based on standard curves generated with known amounts of human MPO purified from leukocytes as described (Hazen, S. L., et al., *J. Biol. Chem.* 271:1861-1867). Purity of isolated MPO was established by demonstrating a RZ of 0.87 ($A_{430}/A_{280}$), SDS PAGE analysis, and in-gel tetramethylbenzidine peroxidase staining (Podrez, E. A., et al., *J. Clin. Invest* 103:1547-1560). Enzyme concentration was determined spectrophotometrically utilizing an extinction coefficient of 89,000 $M^{-1}cm^{-1}$/heme.

Statistical Analysis: Presentation characteristics are depicted as either mean±standard deviation or median (interquartile range) for continuous measures and number and percent for categorical measures. Differences between CAD and control subjects were evaluated with Wilcoxon rank sum or chi-square tests. MPO levels were divided into quartiles for analyses because neither Leukocyte-MPO nor Blood-MPO activity follows a Gaussian distribution. Unadjusted trends for increasing CAD rates with increasing MPO activity were evaluated with the Cochran-Armitage trend test. A modified Framingham Global Risk score was determined utilizing a documented history of hypertension rather than the recorded blood pressure at time of catheterization (Taylor, A. J., et al., *Circulation* 101:1243-1248).

Logistic regression models (SAS System, SAS Institute, Cary N.C.) were developed to calculate odds ratios (OR) estimating the relative risk associated with the combined $2^{nd}$ and $3^{rd}$ quartiles of MPO activity and the highest quartile of MPO activity compared to the lowest quartile. Adjustments were made for individual traditional CAD risk factors (age, gender, diabetes, hypertension, smoking (ever or current), family history, TC, LDLc, HDLc, TG, WBC). Hosmer-Lemeshow goodness of fit tests were employed to evaluate appropriate model fit. Associations among continuous variables were assessed with use of Spearman's rank-correlation coefficient. Associations among categorical variables were assessed using Wilcoxon rank sum tests.

Results

Patient Demographics: The clinical and biochemical characteristics of subjects that participated in this study are shown in Table 1. Subjects with CAD were older, more likely to be male, and more likely to have a history of diabetes, hypertension and smoking. CAD subjects also exhibited increased fasting triglyceride levels, increased use of lipid lowering medications (predominantly statins), aspirin and other cardiovascular medications. Consistent with other studies, Framingham Global Risk Score, absolute neutrophil count and WBC were significantly increased in subjects with CAD (p<0.001 for each; Table 1).

TABLE 1

Clinical and Biochemical Characteristics of Subjects

| Characteristics | c) Control (n = 175) | i) CAD (n = 158) |
|---|---|---|
| Age, y | 55 ± 10 | 64 ± 13*** |
| Gender (female), % | 42 | 20*** |
| Diabetes†, % | 5 | 23*** |
| Hypertension‡, % | 31 | 58*** |
| Family history of CAD, % | 53 | 54 |
| History of smoking, % | 49 | 78*** |
| Current smoking⁂, % | 10 | 9 |
| Any lipid lowering medications, % | 27 | 70*** |

TABLE 1-continued

Clinical and Biochemical Characteristics of Subjects

| Characteristics | c) Control (n = 175) | i) CAD (n = 158) |
|---|---|---|
| Statin, % | 25 | 65*** |
| ASA, % | 71 | 84** |
| ACE Inhibitors, % | 18 | 44*** |
| Beta Blockers, % | 27 | 59*** |
| Calcium Channel Blockers, % | 15 | 24* |
| Total cholesterol, mg/dL¶ | 203 (166-234) | 203 (174-234) |

(i.e. a functional assay), we independently quantified MPO mass per neutrophil in a random subset of subjects (n=111) using an enzyme linked immunosorbent assay. Results observed from this assay significantly correlated (r=0.95) with the activity measurements (data not shown). Since rates for CAD in the second and third quartiles of Leukocyte-MPO appeared comparable (Table 2), they were combined for all further analyses and are referred to as the mid range levels in univariate and multivariate models. As has been seen in other studies, Framingham Global Risk Score and WBC were likewise positively correlated with rates of CAD (Table 2).

TABLE 2

Odds Ratio of Coronary Artery Disease Prevalence According to Myeloperoxidase Levels, White Blood Cell Count and Framingham Global Risk Score

| | Quartile | | | | |
|---|---|---|---|---|---|
| | 1 | 2 | 3 | 4 | for trend |
| Leukocyte-MPO† | | | | | |
| U/mg PMN protein | ≤11.8 | 11.9-15.3 | 15.4-19.8 | >19.9 | |
| CAD Rate | 24/91 (26%) | 35/76 (46%) | 36/83 (43%) | 63/83 (76%) | p < 0.001 |
| Unadjusted OR (CI) | 1.0 | 2.4 (1.2-4.6)** | 2.1 (1.1-4.0)* | 8.8 (4.4-17.5)*** | |
| Model 1ª OR (CI) | | | 8.5 (3.7-19.7)*** | 20.3 (7.9-52.1)*** | |
| Model 2ᵇ OR (CI) | | | 4.2 (2.1-8.1)*** | 11.9 (5.5-25.5)*** | |
| Blood-MPO‡ | | | | | |
| U/PMN × ANC | ≤2.9 | 3.0-4.1 | 4.2-5.7 | ≥5.8 | |
| CAD Rate | 16/91 (18%) | 35/83 (42%) | 41/79 (52%) | 66/80 (83%) | p < 0.001 |
| Unadjusted OR (CI) | 1.0 | 3.4 (1.7-6.8)*** | 5.1 (2.5-10.2)*** | 22.1 (10.0-48.7)*** | |
| Model | | | 3.6 (1.8-7.5)*** | 15.1 (6.2-36.7)*** | |
| Modelᵇ | | | 5.3 (2.7-10.5)*** | 20.4 (8.9-47.2)*** | |
| WBC | | | | | |
| × 10³/mm³ | ≤5.78 | 5.79-7.32 | 7.33-9.02 | ≥9.03 | |
| CAD Rate | 24/85 (28%) | 46/82 (56%) | 38/83 (46%) | 50/83 (60%) | p < 0.001 |
| Unadjusted OR (CI) | 1.0 | 3.2 (1.7-6.2)*** | 2.1 (1.1-4.1)* | 3.9 (2.0-7.3)*** | |
| Adjusted | | | 3.0 (1.6-5.7)*** | 4.3 (2.1-8.9)*** | |
| Framingham | | | | | |
| Global Risk Score | ≤4 | 5-7 | 8-9 | ≥10 | |
| CAD Rate | 25/86 (29%) | 41/114 (36%) | 41/63 (65%) | 51/70 (73%) | p < 0.001 |
| Unadjusted OR (CI) | 1.0 | 1.4 (0.8-2.5) | 4.5 (2.3-9.1)*** | 6.5 (3.2-13.2)*** | |
| Adjustedᶜ OR (CI) | | 1.8 (1.0-3.3) | | 7.8 (3.5-17.5)*** | |

TABLE 1-continued

Clinical and Biochemical Characteristics of Subjects

| Characteristics | c) Control (n = 175) | i) CAD (n = 158) |
|---|---|---|
| LDL cholesterol, mg/dL¶ | 132 (89-144) | 122 (90-146) |
| HDL cholesterol, mg/dL¶ | 49 (40-56) | 43 (36-49) |
| Fasting triglycerides, mg/dL§ | 121 (91-198) | 159 (117-240)*** |
| WBC (×10³/mm³) | 7.4 ± 3.0 | 8.4 ± 3.2*** |
| ANC (×10³/mm³) | 3.8 ± 1.9 | 5.2 ± 2.6*** |
| Framingham Global Risk | 5.5 ± 3.8 | 8.0 ± 3.0*** |

Figure 9:
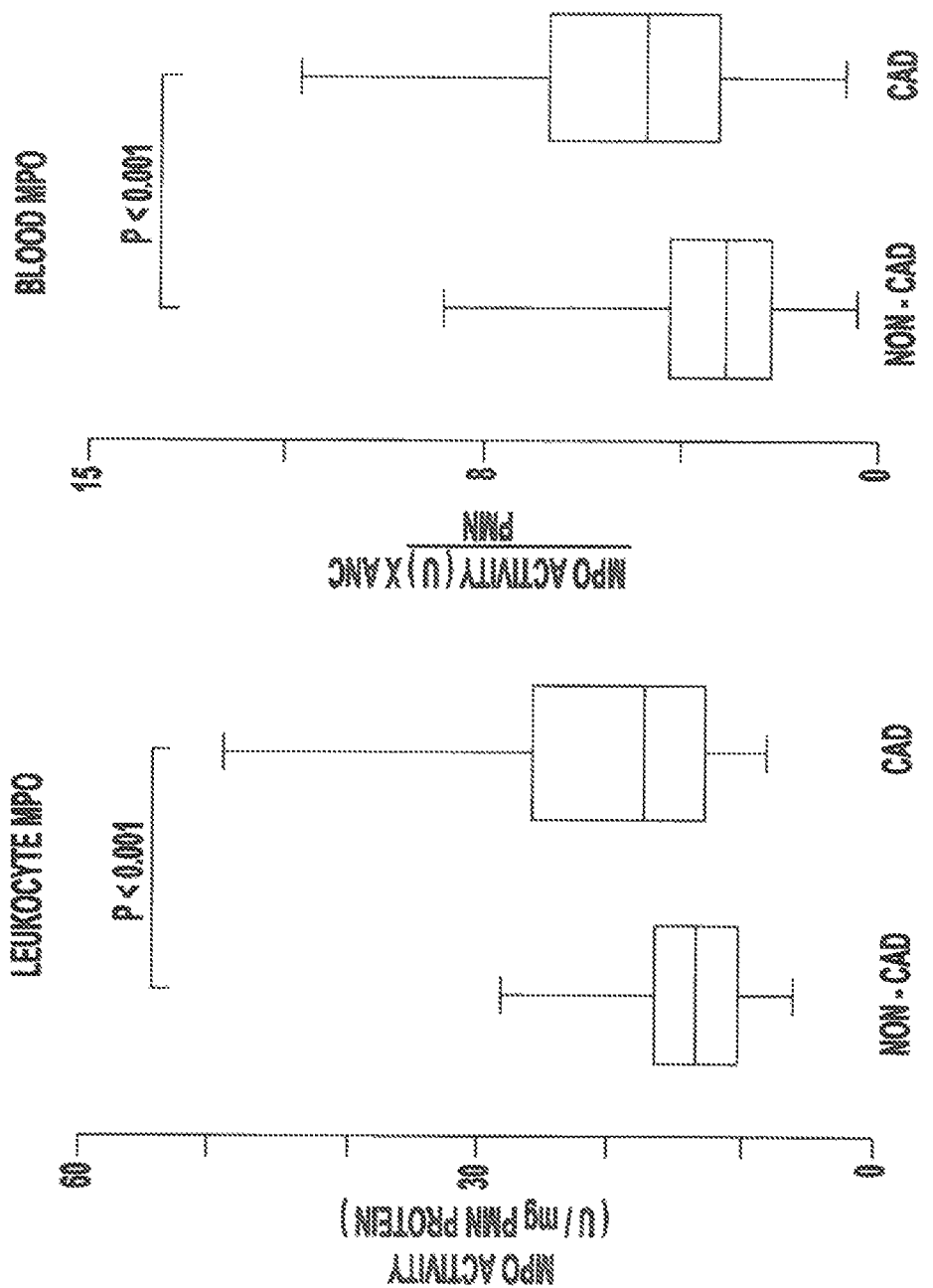
FIG. 9. The content of MPO in isolated leukocytes (Leukocyte-MPO) and per ml of blood (Blood-MPO) were determined in 333 subjects (158 with known coronary artery disease and 175 without angiographically significant CAD) as described under "Methods." Box-whisker plots of MPO levels vs. CAD status are shown. Boxes encompass the $25^{th}$ to $75^{th}$ percentiles. Lines within boxes represent median values. Bars represent the $2.5^{th}$ and $97.5^{th}$ percentiles. ANC, absolute neutrophil count; CAD, coronary artery disease; PMN, polymorphonuclear leukocyte.

Stratification of Leukocyte-MPO, Blood-MPO and White Blood Cell Count Vs. Prevalence of Coronary Artery Disease: To test the hypothesis that individuals with higher levels of MPO have a higher prevalence of CAD, we isolated neutrophils and measured their MPO content. MPO activity per mg of neutrophil protein (Leukocyte-MPO) differed significantly by CAD status with a median of 13.4 U/mg for control subjects vs.18.1 U/mg for CAD patients (p<0.001 for trend, and for difference; FIG. 1). Stratification of Leukocyte-MPO levels by quartiles for the entire cohort revealed a positive correlation with CAD status (p<0.001 for trend) with individuals in the highest quartile having the highest risk (OR(CI), 8.8 (4.4-17.5); Table 2). In addition to quantifying leukocyte MPO content by its catalytic activity The total content of MPO in blood is dependent on both MPO levels per leukocyte as well as the total number of leukocytes. Since neutrophils possess >95% of the MPO content in blood, we estimated the level of MPO per ml of blood (Blood-MPO) by multiplying the content of MPO per neutrophil times the absolute neutrophil count. Rates of CAD were positively correlated with Blood-MPO quartiles (p<0.001 for trend; FIG. 9, Table 2).

Leukocyte-MPO is not Significantly Correlated with Traditional Coronary Artery Risk Factors:

Possible correlations between traditional CAD risk factors and Leukocyte-MPO were next assessed. Leukocyte-MPO levels were independent of age, gender, diabetes, hypertension, smoking (ever or current), WBC, triglycerides LDLc and Framingham Global Risk. Weak negative correlations between Leukocyte-MPO and both total cholesterol (r=−0.15, p=0.005) and HDLc (r=−0.14, p-0.01) were observed. A positive association was seen between Leukocyte-MPO and absolute neutrophil count (r=0.20, p<0.001) and family history of CAD (median leukocyte-MPO with family history=15.9 vs. 14.1 without, p=0.05). Similar correlations were noted for Blood-MPO.

Leukocyte-MPO and Blood-MPO are strongly correlated with coronary artery disease status following adjustments for single and multiple risk factors: To evaluate whether Leukocyte-MPO and Blood-MPO independently associate with CAD status, odds ratios for Leukocyte-MPO and Blood-MPO quartiles were adjusted for individual traditional CAD risk factors. Odds ratios for both the middle ($2^{nd}$ plus $3^{rd}$) and highest ($4^{th}$), relative to the lowest ($1^{st}$), quartiles of both Leukocyte-MPO and Blood-MPO remained highly correlated with CAD status following adjustments for individual traditional CAD risk factors, WBC and Framingham Global Risk Score (data not shown), with odds ratios ranged from 8.4 (CI=4.2-16.9, p<0.001) after adjustment for HDLc to 13.5 (CI=6.3-29.1, p<0.001) after adjustment for smoking. Diabetes, hypertension, smoking, and to a lesser degree age, HDLc, Framingham Global Risk and WBC, also remained significant predictors for CAD status following single factor adjustments. Similar results were observed for Blood-MPO following single factor adjustments for individual traditional CAD risk factors (data not shown).

Figure 10:
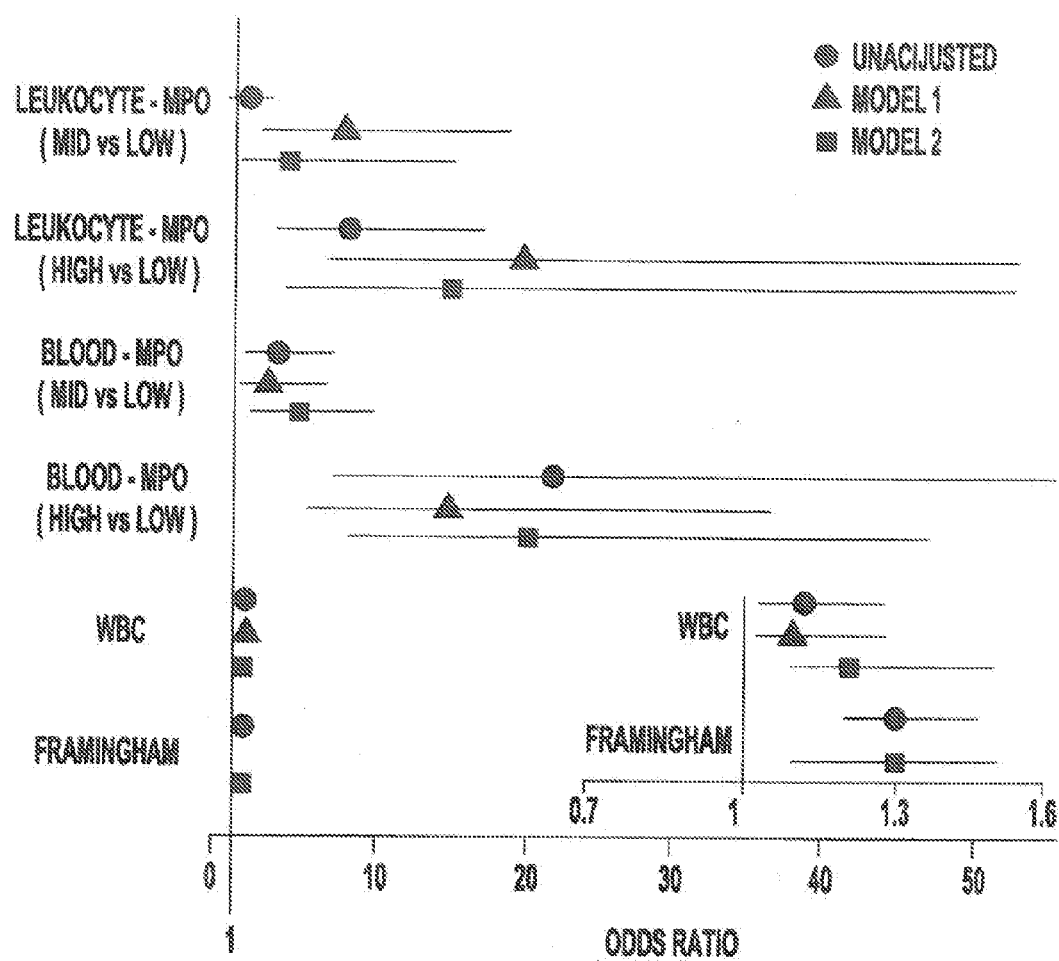
FIG. 10. Model 1—Odds ratios adjusted for risk factors significant following univariate adjustment: age, gender, hypertension, smoking history, HDLc, WBC quartile and MPO quartile. Model 2—Odds ratios adjusted for Framingham Global Risk assessment, WBC and MPO quartile. Closed circles, unadjusted odd ratios. Closed triangles, Model 1. Closed squares, Model 2.

Multivariable regression analyses were then performed using several models (Table 2, FIG. 10). Model 1 examined Leukocyte- and Blood-MPO following simultaneous adjustment for each of the single risk factors that were significantly correlated to CAD in the preceding step (i.e., univariate regression). Leukocyte-MPO remained the strongest predictor of CAD status with an adjusted OR of 8.5 (CI=3.7-19.7, mid vs. low quartile) and 20.3 (CI=7.9-52.1, high vs. low quartile). The adjusted odds ratio for WBC, a marker that predicts increased risk for CAD (2;3;23-25), was 1.1 (CI=1.02-1.21). A second regression model adjusting for Framingham Global Risk Score and WBC yielded ORs for Leukocyte-MPO that were consistent with the large OR observed in Model 1 (mid vs. low OR=4.2; high vs. low OR=11.9). The adjusted OR for Framingham Global Risk Score and WBC were also significant. Blood-MPO likewise remained a strong predictor of CAD status following multivariable adjustments compared to traditional CAD risk factors, Framingham Global Risk Score and WBC (Table 2).

Example 2

Flow Cytometric Analysis of Blood Samples from Subjects with and without CAD

Figure 11:
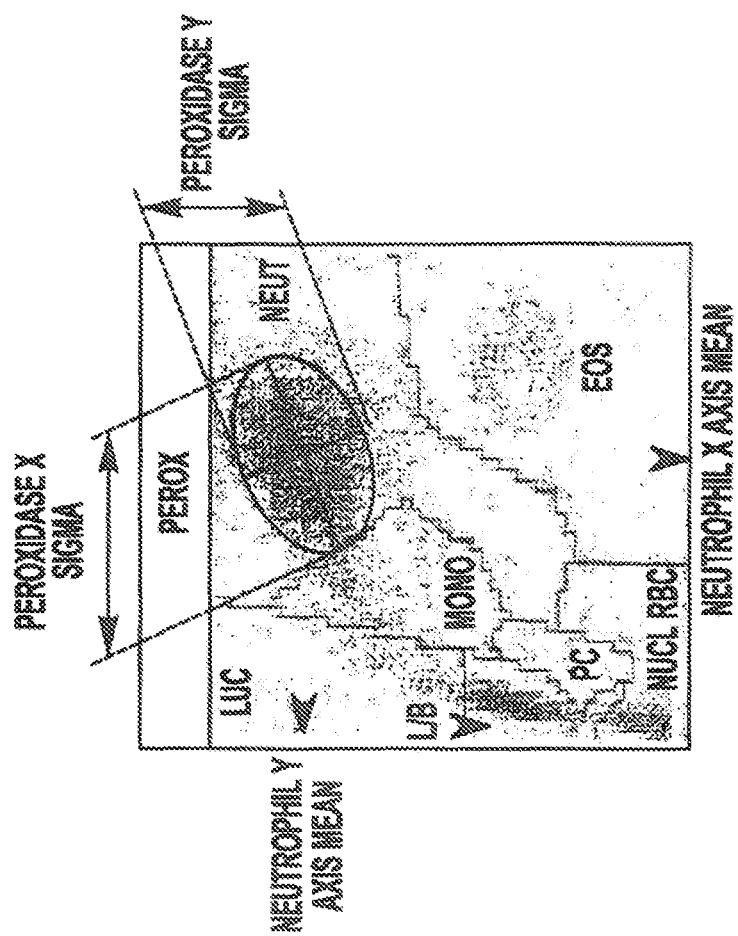
FIG. 11. Cytogram of WBC from an individual whose MPO level per neutrophil is below the average in a population (left panel), and an individual whose MPO level per neutrophil is above average in a population (right panel).

Blood samples from patients whose leukocytes have above normal or below normal levels of MPO were analyzed by flow cytometry. Whole blood from each patient was injected into a hematology analyzer that identifies leukocytes based upon in situ cytochemical peroxidase staining (the Advia 120 from Bayer). In the instrument, whole blood is first lysed and the intact WBCs heated/fixed with formaldehyde. Peroxidase substrates (hydrogen peroxide and a chromophore) are then incubated with the leukocytes, and the resultant stained cells examined by flow cytometry (20 sec overall time between injection of sample and cytogram obtained). The results are shown in FIG. 11. The clusters of cells shown in different colors refer to: 1) Purple—neutrophils; 2) Green—monocytes; 3) Dark Blue—Lymphocytes; 4) Yellow—eosinophils; 5) Turquoise—large unstained cells; 6) White—RBC Ghosts/noise. Based upon these data, the total white blood cell count (WBC) and a differential (% distribution of neutrophils, monocytes, eosinophils and lymphocytes) are reported.

The location of a given cell cluster's position on the cytogram is related to its intensity of light absorption (Y axis—a property that is related to peroxidase activity, and hence, intensity of staining) and light scatter (X axis—a property that is related to both size and granularity/refractive index, properties linked to peroxidase activity and staining).

The left panel illustrates the cytogram from an individual whose MPO level per neutrophil (aka leukocyte-MPO) is below the average in a population (e.g. bottom 25%). The right panel illustrates the location of the cytogram from an individual whose MPO level per neutrophil (aka leukocyte-MPO) is above average in a population (e.g. 50-75$^{th}$%). Note that the location of the neutrophil cluster on the X and Y axes differ, and in general, higher MPO is shifted to the right. Also, the tilt of the major axis of the ellipse that comprises the neutrophil cluster differs. These changes carry information related to the content of MPO within that cell type.

Through use of modeling and standards with known peroxidase content, we can develop standard curves to use this information to identify the relative level of peroxidase per leukocyte. The same kind of analysis is possible for monocytes, the other major cell type in blood with MPO. Peroxidase staining in eosinophils is due to eosinophil peroxidase, a related enzyme to MPO, but a different gene product.

Example 3

Dityrosine Levels in Blood from Human Subjects with and without CAD

The levels of protein-bound dityrosine were measured in blood samples from 112 individuals with CAD and from 128 apparently healthy control subjects. The levels were measured by HPLC with on-line fluorescence detection and were quantified using an external calibration curve generated with synthetic dityrosine. Results were normalized to the content of the precursor amino acid, tyrosine, which was simultaneously quantified by HPLC with on-line diode array detection. The results demonstrated that subjects with CAD had higher levels (50% increased, P<0.001 for comparison of CAD vs. healthy subjects) of dityrosine in their serum than that observed in serum from healthy age and sex-matched subjects.

Example 4

Nitrotyrosine Levels in Blood from Human Subjects with and without CAD

The levels of protein-bound 3-nitrotyrosine were measured in blood samples from the same subjects as Example 3 where 112 individuals with CAD and 128 apparently healthy control subjects were examined. Nitrotyrosine levels were measured by HPLC with on-line electrospray ionization tandem mass spectrometry (LC/ESI/MS/MS) using stable isotope dilution techniques. Results were normalized to the content of the precursor amino acid, tyrosine, which was simultaneously quantified by stable isotope dilution LC/ESI/MS/MS. The results demonstrated that subjects with CAD had higher levels (2.8-fold increased, P<0.001 for comparison of CAD vs. healthy subjects) of nitrotyrosine in their serum than healthy age and sex-matched subjects.

Example 5

Blood Levels of HETEs, HODEs, and F2Isoprostanes in Human Subjects with and without CAD The levels of HETEs, HODEs and F2Isoprostanes were measured in blood samples from the same subjects as Example 3 where 112 individuals with CAD and 128 apparently healthy control subjects were examined. Lipids were measured by HPLC with on-line electrospray ionization tandem mass spectrometry (LC/ESI/MS/MS). Results were normalized to the content of the precursor lipid (arachidonic acid for HETEs and F2Isoprostanes, and linoleic acid for HODEs), which were simultaneously quantified by LC/ESI/MS/MS. The results demonstrated that subjects with CAD had higher levels of each of the oxidation products in their plasma than healthy age and sex-matched subjects. F2Isoprostane levels were 80% greater in plasma obtained from CAD vs. non-CAD subjects, P<0.001; levels of HETEs and HODEs were 60% greater in CAD vs. non-CAD subjects, P<0.001).

Example 6

Blood Levels of MPO-Generated Lipid Oxidation Products in Human Subjects with and without CAD The levels of phospholipid oxidation products shown to be generated by MPO (G-PC and ND-PC, the glutaric and nonanedioic monoesters of 2-lysoPC; HDdiA-PC and HOdiA-PC, the 9-hydroxy-10-dodecenedioic acid and 5-hydroxy-8-oxo-6-octenedioic acid esters of 2-lysoPC; HODA-PC and HOOA-PC, the 9-hydroxy-12-oxo-10-dodecenoic acid and 5-hydroxy-8-oxo-6-octenoic acid esters of 2-lysoPC; KODA-PC and KOOA-PC, the 9-keto-12-oxo-10-dodecenoic acid and 5-keto-8-oxo-6-octenoic acid esters of 2-lysoPC; KDdiA-PC and KOdiA-PC, the 9-keto-10-dodecendioic acid and 5-keto-6-octendioic acid esters of 2-lysoPC; OV-PC and ON-PC, the 5-oxovaleric acid and 9-oxononanoic acid esters of 2-lysoPC; were measured in blood samples from 25 subjects with CAD and 12 apparently healthy control subjects. In addition the levels of cholesterol α-epoxide, 5-cholesten-5α,6α-epoxy-3β-ol; cholesterol β-epoxide, 5-cholesten-5β,6β-epoxy-3β-ol; 7-OH-cholesterol, 5-cholesten-3β,7β-diol; 25-OH cholesterol, 5-cholesten-3β,25-diol; 7-OOH cholesterol, 5-cholesten-3β-ol-7β-hydroperoxide; triol, cholestan-3β,5α,6β-triol.) were measured in blood samples from 25 subjects with CAD and 12 apparently healthy control subjects. Lipids were measured by HPLC with on-line electrospray ionization tandem mass spectrometry (LC/ESI/MS/MS) using established methods. Results were normalized to the content of the precursor lipid (PAPC, 1-hexadecanoyl-2-eicosatetra-5',8',11',14'-enoyl-sn-glycero-3-phosphocholine; PLPC, 1-hexadecanoyl-2-octadecadi-9',12'-enoyl-sn-glycero-3-phosphocholine; or cholesterol), which were simultaneously quantified by LC/ESI/MS/MS. The results demonstrated that subjects with CAD had higher levels (50% to 4-fold, depending upon the lipid) of each of the phospholipid oxidation products in their plasma than healthy age and sex-matched subjects.

What is claimed is:

1. A method for identifying an elevated myeloperoxidase (MPO) concentration in a plasma sample from a human subject with atherosclerotic cardiovascular disease comprising:
    a) contacting a sample with an anti-MPO antibody, wherein said sample is a plasma sample from a human subject having atherosclerotic cardiovascular disease;
    b) spectrophotometrically detecting MPO levels in said plasma sample;
    c) comparing said MPO levels in said plasma sample to a standard curve generated with known amounts of MPO to determine the MPO concentration in said sample; and
    d) comparing said MPO concentration in said plasma sample from said human subject to a control MPO concentration from apparently healthy human subjects, and identifying said MPO concentration in said plasma sample from said human subject as being elevated compared to said control MPO concentration.

2. The method of claim 1, further comprising, prior to step a), centrifuging an anti-coagulated blood sample from said human subject to generate said plasma sample.

* * * * *

UNITED STATES PATENT AND TRADEMARK OFFICE
CERTIFICATE OF CORRECTION

PATENT NO. : 9,581,597 B2  
APPLICATION NO. : 15/135757  
DATED : February 28, 2017  
INVENTOR(S) : Stanley L. Hazen and Renliang Zhang Page 1 of 1

It is certified that error appears in the above-identified patent and that said Letters Patent is hereby corrected as shown below:

In the Specification

In Column 1, Lines 13-16 should read:
This invention was made with government support under HL062526 awarded by the National Institutes of Health. The government has certain rights in the invention.

Signed and Sealed this
Twenty-seventh Day of October, 2020

Andrei Iancu
*Director of the United States Patent and Trademark Office*